United States Patent
Hirzel

(10) Patent No.: US 10,906,682 B2
(45) Date of Patent: Feb. 2, 2021

(54) FOOD PROCESSING SYSTEM, APPARATUS FOR TESTING A FOREIGN OBJECT SENSOR AND A METHOD FOR OPERATING THE FOOD PROCESSING SYSTEM

(71) Applicant: Kellogg Company, Battle Creek, MI (US)

(72) Inventor: Nicholson James Hirzel, Augusta, MI (US)

(73) Assignee: KELLOGG COMPANY, Battle Creek, MI (US)

( * ) Notice: Subject to any disclaimer, the term of this patent is extended or adjusted under 35 U.S.C. 154(b) by 544 days.

(21) Appl. No.: 15/454,148

(22) Filed: Mar. 9, 2017

(65) Prior Publication Data
US 2017/0259949 A1    Sep. 14, 2017

Related U.S. Application Data

(60) Provisional application No. 62/306,182, filed on Mar. 10, 2016.

(51) Int. Cl.
*B65B 57/12*    (2006.01)
*G01N 33/10*    (2006.01)
(Continued)

(52) U.S. Cl.
CPC ............... *B65B 57/12* (2013.01); *B65B 7/02* (2013.01); *B65B 37/16* (2013.01); *B65B 39/007* (2013.01);
(Continued)

(58) Field of Classification Search
CPC .......... B65B 57/12; B65B 57/10; B65B 7/02; B65B 61/26; B65B 37/16; B65B 39/007;
(Continued)

(56) References Cited

U.S. PATENT DOCUMENTS 4,588,091 A *   5/1986   Wade ..................... G01N 33/10
                                                    209/237
4,726,434 A *   2/1988   Mosher ................ G01G 19/393
                                                    177/1
(Continued)

FOREIGN PATENT DOCUMENTS

JP    H02126180    5/1990
JP    H04006489    1/1992
JP    2008233099   10/2008

OTHER PUBLICATIONS

PCT/US2017/021507 International Search Report dated Jul. 6, 2017.

*Primary Examiner* — Thanh K Truong
*Assistant Examiner* — Katie L Gerth
(74) *Attorney, Agent, or Firm* — Honigman LLP; Kathryn D. Doyle, Esq.; Jonathan P. O'Brien

(57) ABSTRACT

A food processing system is disclosed. The food processing system includes a food scaling portion, a food bagging portion and a chute portion connecting the food scaling portion to the food bagging portion. The food processing system also includes a foreign object sensor arranged about the chute portion. The foreign object sensor and the chute portion cooperatively form a foreign object sensing zone within a passage formed by the chute portion that extends along a portion of a length of the chute portion. The food processing system also includes at least one sensor testing conduit extending through one or both of the food scaling portion and the chute portion. An exit opening of the at least one sensor testing conduit is arranged in an opposing relationship with respect to the foreign object sensing zone. A foreign object sensor apparatus for detecting non-foodstuff material is also disclosed. A method is also disclosed.

7 Claims, 23 Drawing Sheets

(51) Int. Cl.
  *B65B 57/10* (2006.01)
  *B65B 7/02* (2006.01)
  *B65B 37/16* (2006.01)
  *B65B 39/00* (2006.01)
  *B65B 61/26* (2006.01)
  *G01F 15/00* (2006.01)
  *G01N 33/02* (2006.01)
  *G01V 3/08* (2006.01)
  *B65B 51/14* (2006.01)
  *B65B 5/02* (2006.01)
  *B65B 25/00* (2006.01)
  *B65B 57/18* (2006.01)

(52) U.S. Cl.
  CPC .............. *B65B 57/10* (2013.01); *B65B 61/26* (2013.01); *G01F 15/00* (2013.01); *G01N 33/02* (2013.01); *G01N 33/10* (2013.01); *G01V 3/08* (2013.01); *B65B 5/022* (2013.01); *B65B 25/00* (2013.01); *B65B 51/146* (2013.01); *B65B 57/18* (2013.01)

(58) Field of Classification Search
  CPC ....... B65B 5/022; B65B 51/146; B65B 25/00; B65B 57/18; B65B 57/00; B65B 57/005; G01N 33/10; G01N 33/02; G01F 15/00; G01V 3/08
  USPC ...................................... 53/469, 167, 77, 507
  See application file for complete search history.

(56) References Cited

U.S. PATENT DOCUMENTS

| | | | | |
|---|---|---|---|---|
| 4,887,475 | A  * | 12/1989 | Austin | B65B 1/04 |
| | | | | 73/866 |
| 7,877,966 | B2 * | 2/2011 | Knoke | B65B 1/36 |
| | | | | 53/451 |
| 10,495,604 | B2 * | 12/2019 | Rigby | G01V 3/107 |
| 2002/0007659 | A1 * | 1/2002 | Bennett | G01V 3/10 |
| | | | | 73/1.01 |
| 2003/0000179 | A1 * | 1/2003 | Nakagawa | B65B 9/2028 |
| | | | | 53/493 |
| 2003/0146836 | A1 * | 8/2003 | Wood | G06K 19/0717 |
| | | | | 340/540 |
| 2005/0198920 | A1 * | 9/2005 | Nakagawa | B65B 9/00 |
| | | | | 53/64 |
| 2006/0277868 | A1 * | 12/2006 | May | B65B 9/15 |
| | | | | 53/417 |
| 2010/0112922 | A1 * | 5/2010 | Freiberger | B65B 9/12 |
| | | | | 452/40 |
| 2011/0047941 | A1 * | 3/2011 | Metzger | B65B 1/36 |
| | | | | 53/469 |
| 2013/0106612 | A1 * | 5/2013 | Licher | B65B 57/14 |
| | | | | 340/665 |
| 2014/0311093 | A1 * | 10/2014 | Huber | B65B 57/02 |
| | | | | 53/415 |

* cited by examiner

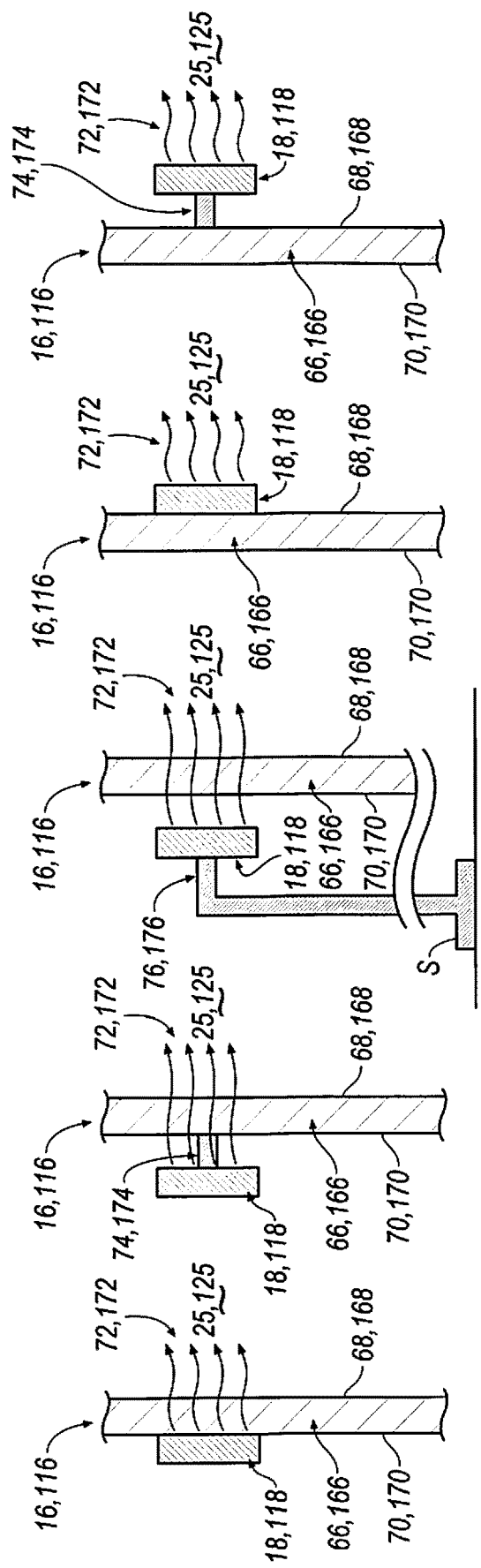

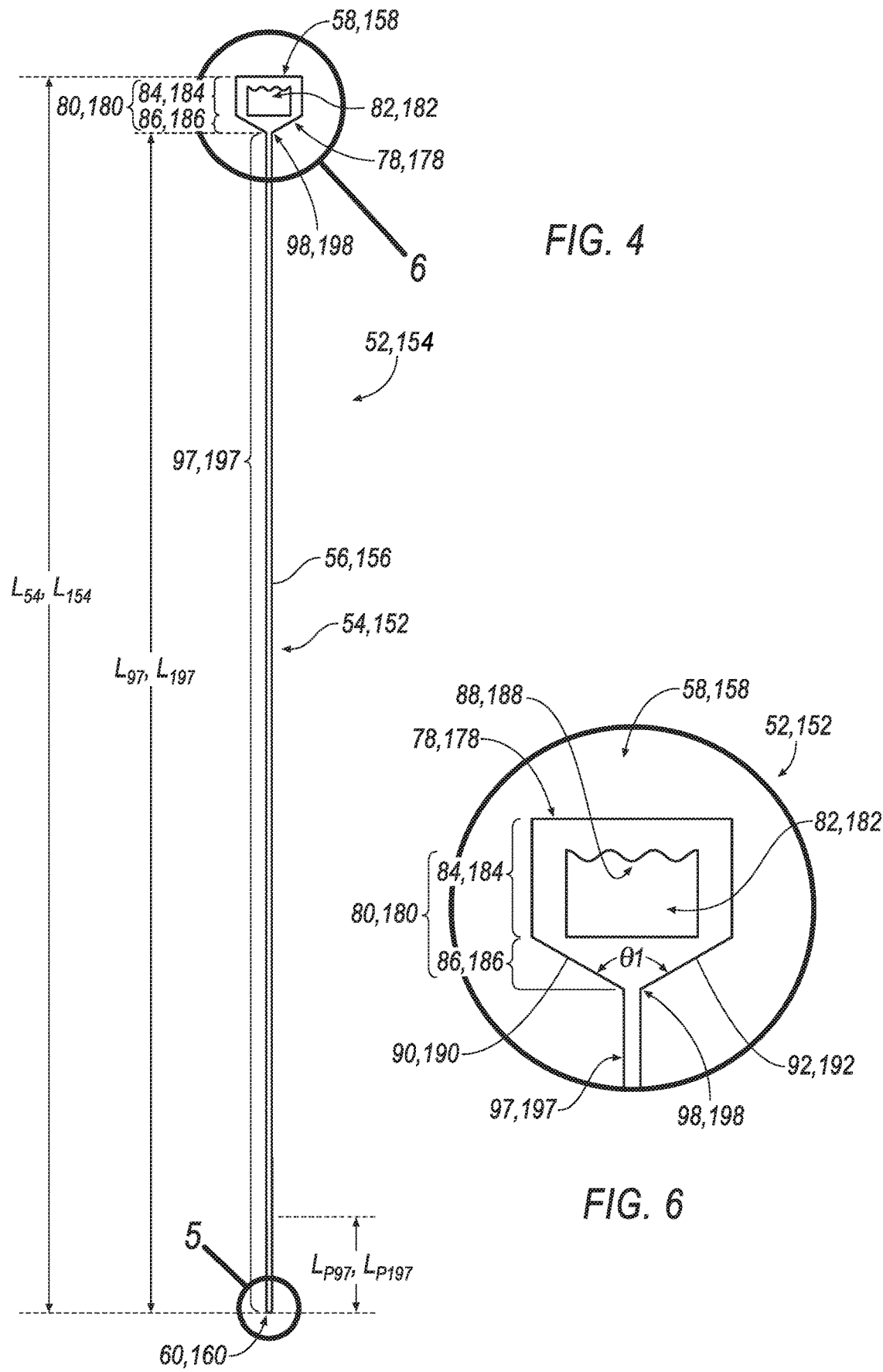

FOOD PROCESSING SYSTEM, APPARATUS FOR TESTING A FOREIGN OBJECT SENSOR AND A METHOD FOR OPERATING THE FOOD PROCESSING SYSTEM

CROSS REFERENCE TO RELATED APPLICATIONS

This application claims the benefit of and priority to U.S. Application Ser. No. 62/306,182 filed Mar. 10, 2016, which is incorporated herein by reference in its entirety.

TECHNICAL FIELD

This disclosure relates to a food processing system, an apparatus for testing a foreign object sensor, and a method for operating the food processing system.

BACKGROUND

Food processing systems are widely used in the manufacturing and packaging of processed foods. Such systems typically include a plurality of sensors that are used to ensure that only foodstuff is disposed in each package once sealed. One such sensor is a metal detector that is used to ensure metal is not inadvertently disposed within a finished package containing foodstuff.

Sensors such as metal detectors used in conjunction with food processing systems are routinely tested to ensure they are functioning properly. For example, a piece of metal may be purposely inserted into processed food upstream of a metal detector at a predetermined location to make sure the metal detector detects the piece of metal. If the sensor detects the metal, the processing system is stopped, the package containing the metal is removed, and the system is restarted. If the metal is not detected, the processing system is stopped so the sensor can be repaired or replaced.

The foregoing process accurately determines whether a metal detector associated with a food processing system is functioning properly. However, implementing the process results in manufacturing delays, as the processing system must be stopped following insertion of the piece of metal to ensure that the package containing the piece of metal is removed which, in turn, results in manufacturing inefficiencies for food manufacturers.

SUMMARY

One aspect of the disclosure provides a food processing system including a food scaling portion, a food bagging portion and a chute portion connecting the food scaling portion to the food bagging portion. The food processing system also includes a foreign object sensor arranged about the chute portion. The foreign object sensor and the chute portion cooperatively form a foreign object sensing zone within a passage formed by the chute portion that extends along a portion of a length of the chute portion. The food processing system also includes at least one sensor testing conduit extending through one or both of the food scaling portion and the chute portion. An exit opening of the at least one sensor testing conduit is arranged in an opposing relationship with respect to the foreign object sensing zone.

In some implementations, the at least one sensor testing conduit includes a body having an inner surface, an outer surface, a proximal end and a distal end. The inner surface defines a passage extending through the body from the proximal end to the distal end. The proximal end forms an entrance opening. The distal end forms the exit opening.

In some examples, the body of the at least one sensor testing conduit is defined by a length extending between the proximal end and the distal end. The length defines the body to have a curvilinear shape.

In some instances, the at least one sensor testing conduit includes two or more sensor testing conduits. The food scaling portion includes a plurality of food scaling channels. Each channel of the plurality of food scaling channels includes a sensor testing conduit of the two or more sensor testing conduits.

In some implementations, the at least one sensor testing conduit is connected to the food scaling portion.

In some examples, the at least one sensor testing conduit is connected to the chute portion.

In some instances, the at least one sensor testing conduit is connected to both of the food scaling portion and the chute portion.

In some implementations, the food processing system also includes a sensor testing implement having a body including an outer surface, a proximal end and a distal end. The body is defined by a length extending between the proximal end and the distal end. The outer surface defines a width or diameter extending through the body. The sensor testing implement is sized for arrangement within the at least one sensor testing conduit such that at least a portion of a length of a the sensor testing implement extending away from the distal end of the sensor testing implement is spatially arrangeable within the foreign object sensing zone upon plunging the sensor testing implement through the at least one sensor testing conduit. At least a portion of the body of the sensor testing implement includes a non-foodstuff material to be detected by the foreign object sensor.

In some examples, the food bagging portion is a vertical form, fill and seal (VFFS) machine.

In some instances, the food processing system includes a controller communicatively coupled to: the food scaling portion, the food bagging portion, the chute portion, the foreign object sensor by one or more lines of communication.

In some implementations, the food processing system includes one or more of: a conveyor portion, a sealed bag portion and a foreign object indicator. The conveyor portion is positioned at least proximate the food bagging portion. The conveyor portion is communicatively coupled to the controller by the one or more lines of communication. The sealed bag processing portion is positioned at least proximate the food bagging portion. The sealed bag processing portion is communicatively coupled to the controller by the one or more lines of communication. The foreign object indicator is communicatively coupled to the controller by the one or more lines of communication.

In some examples, the sealed bag processing portion includes a bag marking device.

In some instances, the bag marking device includes a spray nozzle connected to an ink reservoir.

In some implementations, the sealed bag processing portion includes a bag rejecting device.

In some examples, the bag rejecting device includes a lever or robotic arm.

In some instances, the sealed bag processing portion includes a bag marking device and a bag rejecting device.

In some implementations, the bag marking device includes a spray nozzle connected to an ink reservoir. The bag rejecting device includes a lever or robotic arm.

In some examples, the food processing system includes an actuator communicatively coupled to the controller and connected to the proximal end of the body of the sensor testing implement. The actuator is disposed within, connected to or supported by the food scaling portion.

In some instances, the food processing system includes a button communicatively-coupled to the controller such that upon manually depressing the button, the controller sends a signal to the actuator for causing deployment or retraction of the sensor testing implement through the sensor testing conduit.

In some implementations, the at least one sensor testing conduit is axially aligned with an axial center of a portion of the passage extending through the food filling portion.

In some examples, the at least one sensor testing conduit is offset from an axial center of a portion of the passage extending through the food filling portion.

In some instances, the at least one sensor testing conduit is disposed adjacent an inner surface of a body defining the passage of the food filling portion.

In some implementations, the at least one sensor testing conduit is disposed adjacent an outer surface of a body defining the passage of the food filling portion.

Another aspect of the disclosure provides an apparatus for testing a foreign object sensor including a sensor testing implement having a body including an outer surface, a proximal end and a distal end. The body is defined by a length extending between the proximal end and the distal end. The outer surface defines a width or diameter extending through the body. At least a portion of the body of the sensor testing implement includes a material to be detected by the foreign object sensor.

In some implementations, the proximal end of the sensor testing implement includes a handle portion having a handle body. The handle body includes a grip portion and a sensor testing conduit registration portion.

In some examples, the handle body forms a passage extending through the handle portion. The grip portion includes a finger-receiving serpentine surface that partially defines the passage extending through the handle portion.

In some instances, the sensor testing conduit registration portion includes one or more surface portions sized for mating with a corresponding surface geometry of a proximal end of a sensor testing conduit that receives the sensor testing implement.

In some implementations, the one or more surface portions includes a first surface portion and a second surface portion.

In some examples, the first surface portion and the second surface portion angularly diverge from one another at a first angle.

In some instances, the proximal end of the sensor testing conduit is defined by a first flared surface portion and the second flared surface portion. The first flared surface portion and the second flared surface portion angularly diverge from one another at a second angle.

In some implementations, the first angle is approximately equal to 135°. The second angle is approximately equal to 225°.

In some examples, the sensor testing implement includes a shaft portion. The shaft portion includes a proximal end connected to the handle portion. The distal end of the sensor testing implement is also the distal end of the shaft portion. The shaft portion is defined by a length extending between the proximal end of the shaft portion and the distal end of the shaft portion.

In some instances, the length of the shaft portion of the sensor testing implement is selectively-sized such that when the sensor testing implement is arranged in a fully deployed orientation relative the foreign object sensor, the distal end of the shaft portion is spatially arranged in a spatial center of a foreign object sensing zone of the foreign object sensor.

In some implementations, the at least a portion of the distal end of the sensor testing implement includes the material to be detected by the foreign object sensor.

In some examples, the length of the shaft portion of the sensor testing implement is selectively-sized such that when the sensor testing implement is arranged in a fully deployed orientation, a portion of the length of the shaft portion extending away from the distal end of the shaft portion is spatially arranged in a foreign object sensing zone of the foreign object sensor.

In some instances, the portion of the length of the shaft portion extending away from the distal end of the shaft portion of the sensor testing implement includes the material to be detected by the foreign object sensor.

In some implementations, a portion of or all of the material to be detected by the foreign object sensor is a flexible, non-rigid material.

In some examples, the material to be detected by the foreign object sensor includes a metallic material.

In some instances, the metallic material is a food-grade metallic material selected from the group consisting of: stainless steel, aluminum, copper, carbonized metal, cast iron, galvanized iron, titanium and platinum or gold.

In some implementations, the body of the sensor testing implement further includes a second material that is not detectable by the foreign object sensor.

In some examples, a portion of or all of one or both of the material to be detected by the foreign object sensor and the second material that is not detectable by the foreign object sensor includes a flexible, non-rigid material.

In some instances, the metallic material is a food-grade metallic material selected from the group consisting of: stainless steel, aluminum, copper, carbonized metal, cast iron, galvanized iron, titanium and platinum or gold. The second material is a food-grade plastic material selected from the group consisting of: high density polyethylene (HDPE), low density polyethylene (LDPE), polypropylene (PP) and polyethylene terephthalate (PETE).

In some implementations, at least a portion of the body proximate the distal end of the sensor testing implement includes the material to be detected by the foreign object sensor and the remainder of the body of the sensor testing implement includes the second material that is not detectable by the foreign object sensor.

In some examples, a first portion of the material to be detected by the foreign object sensor is exposed to surrounding atmosphere. A second portion of the material to be detected by the foreign object sensor is disposed adjacent the second material that is not detectable by the foreign object sensor, and, therefore, is not exposed to surrounding atmosphere.

In some instances, the material to be detected by the foreign object sensor is completely surrounded by the second material that is not detectable by the foreign object sensor, and, therefore, the material to be detected by the foreign object sensor is not exposed to surrounding atmosphere.

In some implementations, the material to be detected by the foreign object sensor is a metal ball or ball bearing that is secured to and received within a corresponding pocket or recess defined by the second material that is not detectable by the foreign object sensor.

In some examples, the material to be detected by the foreign object sensor is connected to the second material that is not detectable by the foreign object sensor by way of a connection selected from the group consisting of: a mechanical connection, a friction-fit connection, an adhesive connection and an over-molding connection.

In some instances, a first portion of the outer surface of the sensor testing implement proximate to and extending away from the distal end of the sensor testing implement is defined by a first visual indicator communicating to a user that the sensor testing implement should be further plunged through an entrance opening of a sensor testing conduit. A second portion of the outer surface of the sensor testing implement proximate to and extending away from the proximal end of the sensor testing implement is defined by a second visual indicator different from the first visual indicator for communicating to the user that further plunging of the sensor testing implement through the entrance opening of the sensor testing conduit should be selectively ceased at any time because the sensor testing implement has been sufficiently inserted into the entrance opening of the sensor testing conduit such that the material to be detected by the foreign object sensor has been spatially arranged relative the foreign object sensor.

In some implementations, the first visual indicator is a first color. The second visual indicator is a second color. The second color may be different from the first color.

Another aspect of the disclosure provides a method including forming a bag having a sealed lower end and an open, non-sealed upper end. The method includes metering an amount of foodstuff material into the bag; while the amount of foodstuff material is metered into the bag, utilizing a foreign object sensor for monitoring for the presence of a sensor testing implement deliberately arranged in a foreign object sensing zone formed by the foreign object sensor.

In some instances, the method may also include: utilizing a food scaling portion for metering the amount of foodstuff material; utilizing a food bagging portion for forming the bag; and utilizing a chute portion for guiding the amount of foodstuff material. The chute portion connects the food scaling portion to the food bagging portion. The method may also include arranging the foreign object sensor about the chute portion.

In some examples, after concluding a period of metering the amount of foodstuff material into the bag and during the monitoring for the presence of the sensor testing implement deliberately arranged in the foreign object sensing zone, if the foreign object sensor does not detect the presence of the sensor testing implement deliberately arranged in the foreign object sensing zone, the method further includes: sealing the open, non-sealed upper end of the bag and conveying the sealed bag to another location.

In some implementations, after concluding a period of metering the amount of foodstuff material into the bag and during the monitoring for the presence of the sensor testing implement deliberately arranged in the foreign object sensing zone, if the foreign object sensor detects the presence of the sensor testing implement deliberately arranged in the foreign object sensing zone, the method further includes sealing the open, non-sealed upper end of the bag and processing the sealed bag as a reject bag.

In some instances, the processing the sealed bag step includes marking the reject bag.

In some examples, the marking step includes spraying ink upon the reject bag.

In some implementations, the marking step includes applying a tag to the reject bag.

In some instances, the processing the sealed bag step includes removing the reject bag from a conveyor portion.

In some examples, the processing the sealed bag step includes marking the reject bag and removing the reject bag from a conveyor portion.

In some instances, the marking step includes spraying ink upon the reject bag.

In some examples, the marking step includes: applying a tag to the reject bag.

In some implementations, after concluding a period of metering the amount of foodstuff material into the bag and during the monitoring for the presence of the sensor testing implement deliberately arranged in the foreign object sensing zone, if the foreign object sensor detects the presence of the sensor testing implement deliberately arranged in the foreign object sensing zone, the method further includes actuating an alarm.

The details of one or more implementations of the disclosure are set forth in the accompanying drawings and the description below. Other aspects, features, and advantages will be apparent from the description and drawings, and from the claims.

DESCRIPTION OF DRAWINGS

The various embodiments provided herein are described in detail with reference to the following figures. The drawings are provided for purposes of illustration only and merely depict typical or example embodiments. These drawings are provided to facilitate the reader's understanding of the invention and shall not be considered limiting of the breadth, scope, or applicability of the embodiments. It should be noted that for clarity and ease of illustration these drawings are not necessarily made to scale.

FIGS. 3A-3E are exemplary cross-sectional views of a portion of the food processing system according to line 3 of FIG. 1 or FIG. 2.

FIGS. 4 and 4a are views of an exemplary sensor testing implement.

FIG. 6 is an enlarged view of a portion of the sensor testing implement according to line 6 of FIG. 4.

DETAILED DESCRIPTION

Figure 1:
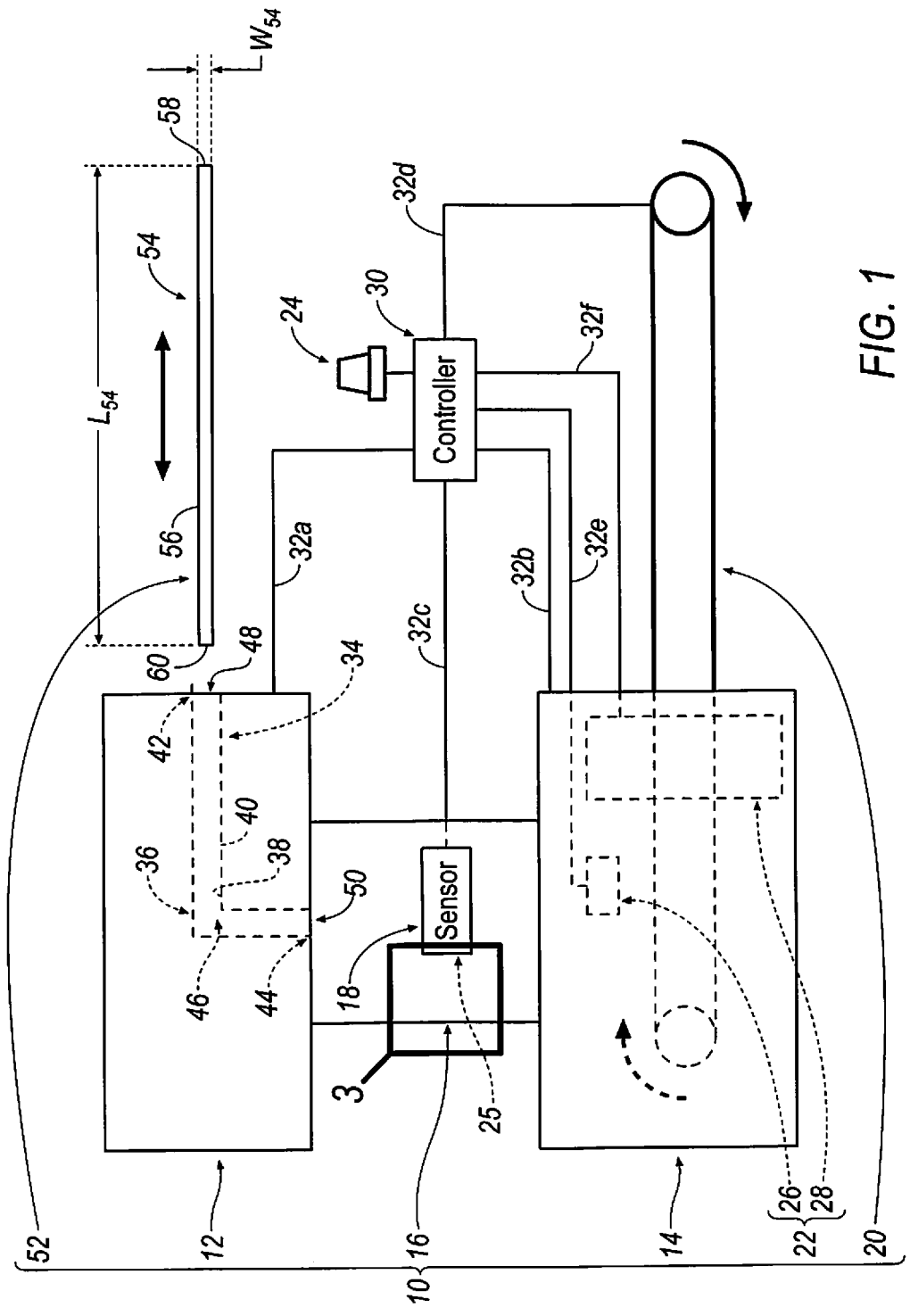
FIG. 1 is a view of an exemplary food processing system.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Food processing systems, an apparatus for testing a foreign object sensor, and a method for operating the food processing system are described in the present disclosure. The food processing systems include a foreign object sensor that detects one or more non-foodstuff objects being passed from a first portion of the food processing system to a second portion of the food processing system.

Figure 2:
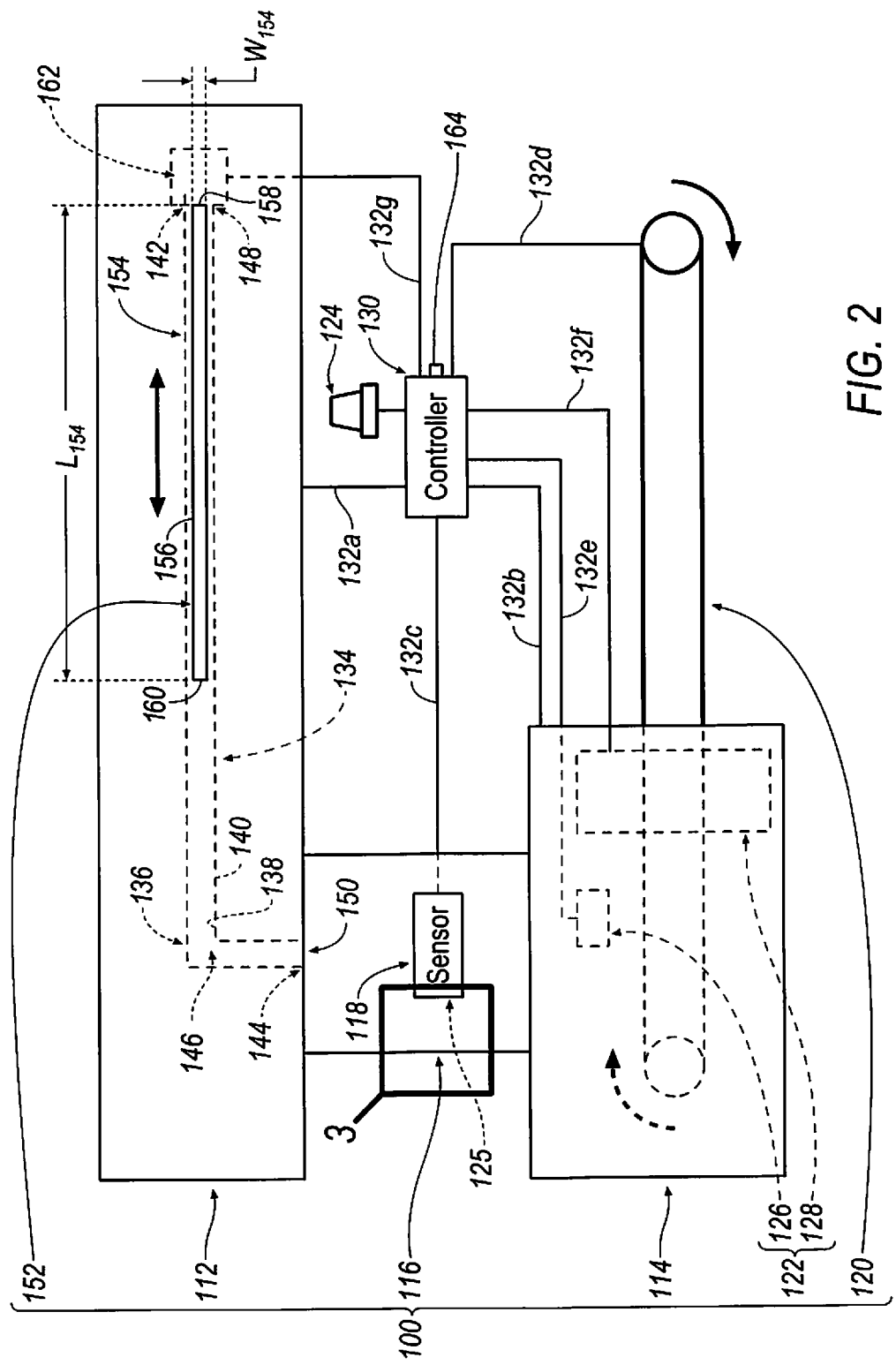
FIG. 2 is a view of an exemplary food processing system.

Referring to FIG. 1, an exemplary food processing system is shown generally at 10. Referring to FIG. 2, another exemplary food processing system is shown generally at 100. Both of the food processing systems 10, 100 include a food metering and/or scaling portion 12, 112 and a food collecting and/or bagging portion 14, 114. A filling and/or chute portion 16, 116 connects the scaling portion 12, 112 to the food bagging portion 14, 114. In this regard, the chute portion 16, 116 may communicate with the scaling portion 12, 112 and the food bagging portion 14, 114, thus allowing the scaling portion 12, 112 to indirectly communicate with the bagging portion 14, 114.

The scaling portion 12, 112 meters a desired amount of foodstuff material F (see, e.g., FIGS. 12A-12C, 13A-13C, 14A-14C) that is subsequently received at the food bagging portion 14, 114. The chute portion 16, 116 guides the metered amount of the foodstuff material F from the scaling portion 12, 112 to the food bagging portion 14, 114.

Prior to receiving the metered amount of foodstuff material F, the food bagging portion 14, 114 forms a bag (see, e.g., B in FIGS. 12A-12C, 13A-13C, and 14A-14C). After the bag B is formed, the metered amount of foodstuff material F, is received within the bag B. The food bagging portion 14, 114 the seals the bag B. In some instances, the food bagging portion 14, 114 may be a vertical-form-fill-and-seal (VFFS) machine.

In some examples, the chute portion 16, 116 may be considered to be a component that forms part of, and, as such, extends away from one of the scaling portion 12, 112 or the food bagging portion 14, 114. In other examples, the chute portion 16, 116 may be a structural portion that is not necessarily considered to be a component of either of the scaling portion 12, 112 or the food bagging portion 14, 114 (i.e., the chute portion 16, 116 may be a structural component that is independent of the scaling portion 12, 112 and the food bagging portion 14, 114).

A foreign object sensor 18, 118 may be: directly connected to (see, e.g., FIGS. 3A, 3D), indirectly connected to (see, e.g., FIGS. 3B, 3E), or positioned proximate (see, e.g., FIG. 3C) the chute portion 16, 116. Furthermore, the foreign object sensor 18, 118 may be positioned exterior of (see, e.g., FIGS. 3A-3C) or disposed within (see, e.g., FIGS. 3D-3E) the chute portion 16, 116.

The foreign object sensor 18, 118 detects the presence of non-foodstuff material F' (see, e.g., FIGS. 5A-5C) spatially arranged anywhere in the stream of the foodstuff material F (such as, e.g., within or passing through the chute portion 16, 116 that contains the stream of the foodstuff material F). The non-foodstuff material F' may include one or more foreign objects. The one or more foreign objects F may include, for example, metallic material M1 (see, e.g., FIGS. 5A-5C). Accordingly, during operation of the food processing system 10, 100, the foreign object sensor 18, 118 continuously monitors for the presence of non-foodstuff material F' that could potentially be spatially arranged within or be passing through the chute portion 16, 116.

As will be described in the following disclosure at FIGS. 12A-12C, 13A-13C and 14A-14C, the design of the exemplary food processing systems 10, 100 permits selective insertion (see, e.g., FIGS. 12A-12B, 13A-13B, 14A-14B) and subsequent withdrawal (see, e.g., FIGS. 12B-12C, 13B-13C, 14B-14C) of non-foodstuff material F' within the chute portion 16, 116. By permitting selective insertion and subsequent withdrawal of non-foodstuff material F' within the chute portion 16, 116, the foreign object sensor 18, 118 may be tested, as desired (e.g., on a discreet basis or periodic basis, which may occur during operation of the foodstuff processing systems 10, 100). As a result of the ability to selectively insert and subsequently withdrawal non-foodstuff material F' within the chute portion 16, 116, the exemplary food processing systems 10, 100 may be permitted to continuously operate without undesirably experiencing delay or to machine down time that would otherwise interrupt the food manufacturing and/or food processing process.

Referring to FIG. 1, in addition to the food scaling portion 12, the food bagging portion 14, the chute portion 16, and the foreign object sensor 18, the food processing system 10 may optionally include a conveyor portion 20, a sealed bag processing portion 22, and a foreign object indicator 24. The conveyor portion 20 transports one or more foodstuff bags B away from the food bagging portion 14. The sealed bag processing portion 22 may include one or more of a bag marking device 26 (see also FIGS. 12A-12C and 14A-14C) and a bag rejecting device 28 (see also FIGS. 13A-13C and 14A-14C). As seen, for example, in FIGS. 12B-12C and 14B-14C, after the food bagging portion 14 seals a bag B containing foodstuff material F, the sealed bag processing portion 22 may provide a marking (see, e.g., "X" in FIGS. 12C and 14C) upon a rejected foodstuff bag B' of the one or more foodstuff bags B. As seen, for example, in FIGS. 13B-13C and 14B-14C, after the food bagging portion 14 seals a bag B containing foodstuff material F, the bag rejecting device 28 removes a rejected foodstuff bag B' of the one or more foodstuff bags B from the conveyor portion 20.

Furthermore, the food processing system 10 may include a controller 30. The controller 30 may be a computing resource such as, for example, a digital computer, and may include, but is not limited to: one or more electronic digital processors or central processing units (CPUs) in communication with one or more storage resources (e.g., memory, flash memory, dynamic random access memory (DRAM), phase change memory (PCM), and/or disk drives having spindles)).

The controller 30 is communicatively coupled (by, e.g., one or more wired or wireless lines of communication 32a, 32b, 32c, 32d, 32e, 32f) to at least one of the food scaling portion 12, the food bagging portion 14, the chute portion 16, the foreign object sensor 18, the conveyor portion 20, the sealed bag processing portion 22, the foreign object indicator 24, the bag marking device 26 and the bag rejecting device 28.

The food processing system 10 also includes a sensor testing conduit 34. The sensor testing conduit 34 may be defined by a body 36 having an inner surface 38, an outer surface 40, a proximal end 42 and a distal end 44. The body 36 forming the sensor testing conduit 34 may be defined to include a linear shape, a non-linear shape, or a curved shape such that the body 36 may include one or more segments that are linear or non-linear (i.e., a "curvilinear" shape as seen, for example, in FIGS. 1, 2, 11A-11B, 12A-12C, 13A-13C, 14A-14C). The inner surface 38 defines a passage 46 extending through the body 36 from the proximal end 42 to the distal end 44. The proximal end 42 forms an entrance opening 48 in the body 36. The distal end 44 forms an exit opening 50 in the body 36. Furthermore, the body 36 may be defined by a length $L_{36}$ (see, e.g., FIG. 7) extending between the proximal end 42 and the distal end 44.

In some instances, the sensor testing conduit 34 may be connected to the food scaling portion 12. In other arrangements, the sensor testing conduit 34 may be connected to the chute portion 16. In another example, the sensor testing conduit 34 may be connected to both of the food scaling portion 12 and the chute portion 16.

The sensor testing conduit 34 guides a sensor testing implement 52 (see also, FIG. 4). The sensor testing implement 52 includes a body 54 having an outer surface 56, a proximal end 58 and a distal end 60. The body 54 may be defined by a length $L_{54}$ extending between the proximal end 58 and the distal end 60. The outer surface 56 may define a width or diameter $W_{54}$ extending through the body 54. As will be described in the following disclosure at FIGS. 12A-12C, 13A-13C and 14A-14C, depending upon the connection or arrangement of the sensor testing conduit 34 relative one or more of the food scaling portion 12, the food bagging portion 14 and the chute portion 16 as described above, at least the exit opening 50 of the body 36 of the sensor testing conduit 34 is arranged in manner such that the distal end 60 of the sensor testing implement 52 may spatially traverse a foreign object sensing zone 25. The foreign object sensing zone 25 may be provided by an arrangement of the foreign object sensor 18 relative the chute portion 16. In particular, the foreign object sensing zone 25 may be at least partially aligned with the foreign object sensor 18.

Referring to FIG. 2, in addition to the food scaling portion 112, the food bagging portion 114, the chute portion 116 and the foreign object sensor 118, the food processing system 100 may optionally include a conveyor portion 120, a sealed bag processing portion 122, and a foreign object indicator 124. The conveyor portion 120 transports one or more foodstuff bags B away from the food bagging portion 114.

The sealed bag processing portion 122 may include one or more of a bag marking device 126 (see also FIGS. 12A-12C and 14A-14C) and a bag rejecting device 128 (see also FIGS. 13A-13C and 14A-14C). As seen, for example, in FIGS. 12B-12C and 14B-14C, after the food bagging portion 114 seals a bag B containing foodstuff material F, the sealed bag processing portion 122 may provide a marking (see, e.g., "X" in FIGS. 12C and 14C) upon a rejected foodstuff bag B' of the one or more foodstuff bags B. As seen, for example, in FIGS. 13B-13C and 14B-14C, after the food bagging portion 114 seals a bag B containing foodstuff material F, the bag rejecting device 128 removes a rejected foodstuff bag B' of the one or more foodstuff bags B from the conveyor portion 120.

Furthermore, the food processing system 100 may include a controller 130. The controller 130 may be a computing resource such as, for example, a digital computer, and may include, but is not limited to: one or more electronic digital processors or central processing units (CPUs) in communication with one or more storage resources (e.g., memory, flash memory, dynamic random access memory (DRAM), phase change memory (PCM), and/or disk drives having spindles)).

The controller 130 is communicatively coupled (by, e.g., one or more wired or wireless lines of communication 132$a$, 132$b$, 132$c$, 132$d$, 132$e$, 132$f$, 132$g$) to at least one of the food scaling portion 112, the food bagging portion 114, the chute portion 116, the foreign object sensor 118, the conveyor portion 120, the sealed bag processing portion 122, the foreign object indicator 124, the bag marking device 126, the bag rejecting device 128 and an actuator 162, which will be described below in the following disclosure.

The food processing system 100 also includes a sensor testing conduit 134. The sensor testing conduit 134 may be defined by a body 136 having an inner surface 138, an outer surface 140, a proximal end 142 and a distal end 144. The body 136 forming the sensor testing conduit 134 may be defined to include a linear shape, a non-linear shape, or a curved shape such that the body 136 may include one or more segments that are linear or non-linear (i.e., a "curvilinear" shape as seen, for example, in FIGS. 1, 2, 11A-11B, 12A-12C, 13A-13C, 14A-14C). The inner surface 138 defines a passage 146 extending through the body 136 from the proximal end 142 to the distal end 144. The proximal end 142 forms an entrance opening 148 in the body 136. The distal end 144 forms an exit opening 150 in the body 136. Furthermore, the body 136 may be defined by a length $L_{136}$ (see, e.g., FIG. 7) extending between the proximal end 142 and the distal end 144.

In some instances, the sensor testing conduit 134 may be connected to the food scaling portion 112. In other arrangements, the sensor testing conduit 134 may be connected to the chute portion 116. In another example, the sensor testing conduit 134 may be connected to both of the food scaling portion 112 and the chute portion 116.

The sensor testing conduit 134 guides a sensor testing implement 152 (see also, FIG. 4). The sensor testing implement 152 includes a body 154 having an outer surface 156, a proximal end 158 and a distal end 160. The body 154 may be defined by a length $L_{154}$ extending between the proximal end 158 and the distal end 160. The outer surface 156 may define a width or diameter $W_{154}$ extending through the body 154. As will be described in the following disclosure at FIGS. 12A-12C, 13A-13C and 14A-14C, depending upon the connection or arrangement of the sensor testing conduit 134 relative one or more of the food scaling portion 112, the food bagging portion 114 and the chute portion 116 as described above, at least the exit opening 150 of the body 136 of the sensor testing conduit 134 is arranged in manner such that the distal end 160 of the sensor testing implement 152 may spatially traverse a foreign object sensing zone 125 provided by an arrangement of the foreign object sensor 118 relative the chute portion 116.

Additionally, the food processing system 100 may include an actuator 162. The actuator 162 is connected to the proximal end 158 of the body 154 of the sensor testing implement 152. In some instances, the actuator 162 may be disposed within, connected to, and/or supported by the food scaling portion 112.

Inclusion of the actuator 162 permits the exemplary food processing system 100 to be operated in an automated or automatic fashion. In an example, the controller 130 may be programmed in a manner to send a signal to the actuator 162 in order to cause the actuator 162 to deploy (e.g., insert) the sensor testing implement 152 through the sensor testing conduit 134 such that the sensor testing implement 152 may spatially traverse the foreign object sensing zone 125 of the foreign object sensor 118. After deployment of the sensor testing implement 152 through the sensor testing conduit 134, the controller 130 may subsequently send a signal to the actuator 162 for retracting (e.g., withdrawing) the sensor testing implement 152 through the sensor testing conduit 134 such that the sensor testing implement 152 does not spatially traverse the foreign object sensing zone 125.

Conversely, as seen and described above, the exemplary food processing system 10 may be manually operated such that a person may grasp the proximal end 58 of the body 54 of the sensor testing implement 52 in order to manually deploy (e.g., insert) the sensor testing implement 52 within, and subsequently manually retract (e.g., withdraw) the sensor testing implement 52 from, the sensor testing conduit 34. Although the exemplary food processing system 100 may be operated in an automated or automatic fashion as described above, the exemplary food processing system 100 may alternatively or selectively be operated in a manual fashion by, for example, permitting a person to depress a button 164 communicatively-coupled to the controller 130 such that upon manually depressing the button 164, the controller 130 may send a signal to the actuator 162 for causing deployment or retraction of the sensor testing implement 152 through the sensor testing conduit 134.

In a first example, the sensor testing implement 152 may remain in a deployed orientation so long as an operator manually depresses the button 164. When the operator no longer manually applies pressure to, and, therefore, manually releases the button 164, the sensor testing implement 152 may be returned to a retracted orientation. In another example, a person may manually depress and then immediately manually release the button 164 in order to manually deploy the sensor testing implement 152. When the person wishes to manually retract the sensor testing implement 152 from the deployed position, the person may once again manually depress and then immediately manually release the button 164. In yet another example, upon manually depressing the button 164, the sensor testing implement 152 may be manually deployed and then remain manually deployed for a predetermined period of time as determined by a timer program executed by the controller 130 such that the person does not need to manually press-and-hold the button 164 or depress the button 164 a plurality of times as described above for causing movement of the sensor testing implement 152; therefore, in such an implementation, although the deployment of the sensor testing implement 152 is manually initiated, the controller 130 may automatically cause retraction of the sensor testing implement (i.e., such a methodology may be deemed as a hybrid, manual-and-automatic process for deploying and subsequently retracting the sensor testing implement 152).

Referring to FIGS. 3A-3E, a plurality of exemplary arrangements of the foreign object sensor 18, 118 relative the chute portion 16, 116 are shown. The chute portion 16, 116 generally includes a body 66, 166 having an inner surface 68, 168 and an outer surface 70, 170. The inner surface 68, 168 generally defines a passage 72, 172 extending through the body 66, 166 of the chute portion 16, 116. The foreign object sensing zone 25, 125 is shown within the passage 72, 172 and is substantially aligned with a spatial location of the foreign object sensor 18, 118 relative the chute portion 16, 116.

As seen in FIGS. 3A-3C, the foreign object sensor 18, 118 may be positioned exterior of the body 66, 166 of the chute portion 16, 116. When positioned exterior of the body 66, 166 of the chute portion 16, 116, the foreign object sensor 18, 118 senses non-foodstuff material F' arranged within foreign object sensing zone 25, 125 (i.e., the material defining the body 66, 166 of the chute portion 16, 116 does not prevent the foreign object sensor 18, 118 from sensing non-foodstuff material F' arranged within the foreign object sensing zone 25, 125). Referring to FIGS. 3D-3E, the foreign object sensor 18, 118 may be positioned within the passage 72, 172 of the chute portion 16, 116 for sensing non-foodstuff material F' arranged within foreign object sensing zone 25, 125.

In some instances, as seen in FIGS. 3A and 3D, the foreign object sensor 18, 118 may be disposed directly adjacent the body 66, 166 of the chute portion 16, 116. As seen in FIG. 3A, the foreign object sensor 18, 118 may be disposed directly adjacent the outer surface 70, 170 of the body 66, 166 of the chute portion 16, 116. Conversely, as seen in FIG. 3D, the foreign object sensor 18, 118 may be disposed directly adjacent the inner surface 68, 168 of the body 66, 166 of the chute portion 16, 116.

In other examples, as seen in FIGS. 3B and 3E, the foreign object sensor 18, 118 may be arranged in a spaced-apart relationship with respect to the body 66, 166 of the chute portion 16, 116. As seen in FIG. 3B, the foreign object sensor 18, 118 may be arranged in a spaced-apart relationship with respect to the outer surface 70, 170 of the body 66, 166 of the chute portion 16, 116. Conversely, as seen in FIG. 3E, the foreign object sensor 18, 118 may be arranged in a spaced-apart relationship with respect to the inner surface 68, 168 of the body 66, 166 of the chute portion 16, 116. In some instances, a bracket 74, 174 may be disposed between the foreign object sensor 18, 118 and the body 66, 166 of the chute portion 16, 116 for indirectly connecting the foreign object sensor 18, 118 to the body 66, 166 of the chute portion 16, 116 in a spaced-apart relationship.

In yet another example as seen in FIG. 3C, the foreign object sensor 18, 118 may be arranged in a spaced-apart relationship with respect to the body 66, 166 of the chute portion 16, 116. Unlike the exemplary embodiments described above at FIGS. 3B and 3E, the foreign object sensor 18, 118 of the exemplary embodiment of FIG. 3C is not indirectly connected to the body 66, 166 of the chute portion 16, 116 with an intervening structure such as, for example, a bracket 74, 174. Furthermore, the foreign object sensor 18, 118 of the exemplary embodiment of FIG. 3C is not connected to the body 66, 166 of the chute portion 16, 116, in some instances, the foreign object sensor 18, 118 may be spatially supported by a stand 76, 176 that is disposed upon an underlying surface, S, such that the foreign object sensor 18, 118 may be said to be selectively positioned proximate the chute portion 16, 116.

Referring to FIG. 4, an exemplary sensor testing implement 52, 152 is shown. At least a portion of the body 54, 154 of the sensor testing implement 52, 152 includes a non-foodstuff material F' (see, e.g., first material M1 in FIGS. 5A, 5B, 5C) to be detected by the foreign object sensor 18, 118. Furthermore, a portion of or all of the material (see, e.g., first material M1 and/or second material M2 in FIGS. 5A, 5B, 5C) defining the body 54, 154 of the sensor testing implement 52, 152 may be flexible (i.e., non-rigid) in order to permit the body 54, 154 to bend as the sensor testing implement 52, 152 is deployed or retracted within the sensor testing conduit 34, 134 (e.g., the sensor testing conduit 34, 134 may be defined to include a non-linear, curved shape (i.e., the sensor testing conduit 34, 134 may be "curvilinear") as seen, for example, in FIGS. 1, 2, 11A-11B, 12A-12C, 13A-13C, 14A-14C).

Figure 5C:
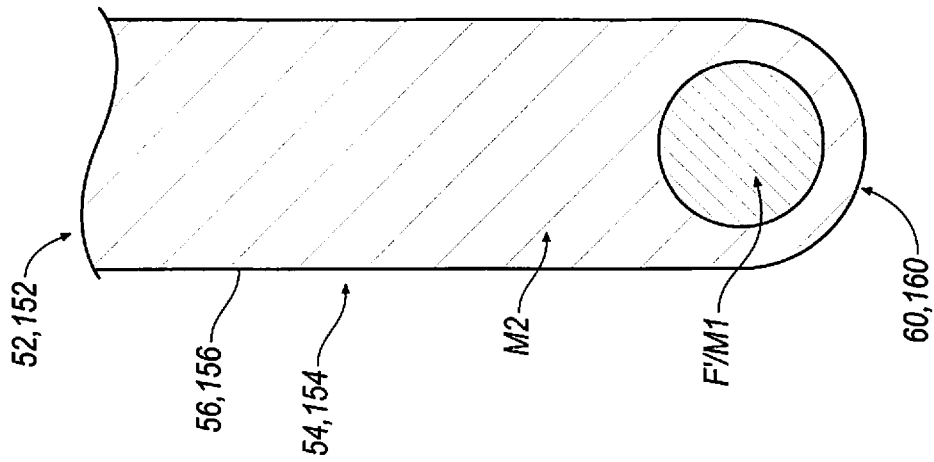
FIGS. 5A-5C are exemplary cross-sectional views of a portion of the sensor testing implement according to line 5 of FIG. 4.
Figure 5B:
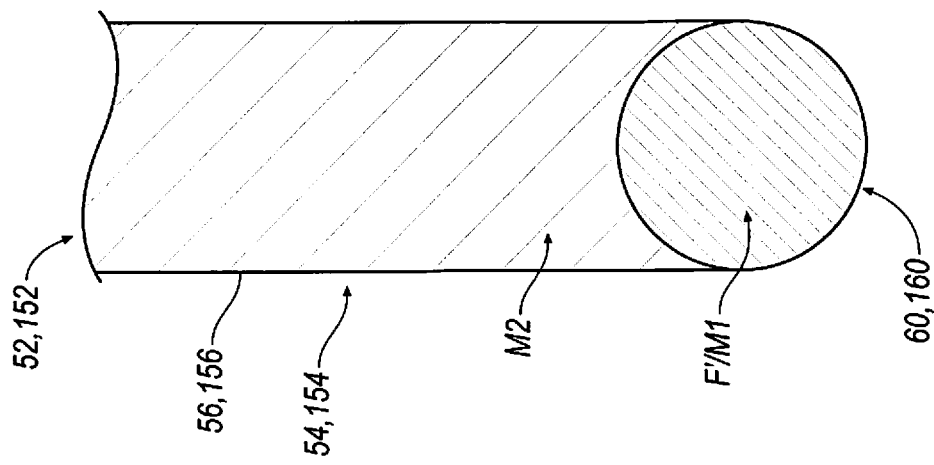
Figure 5A:
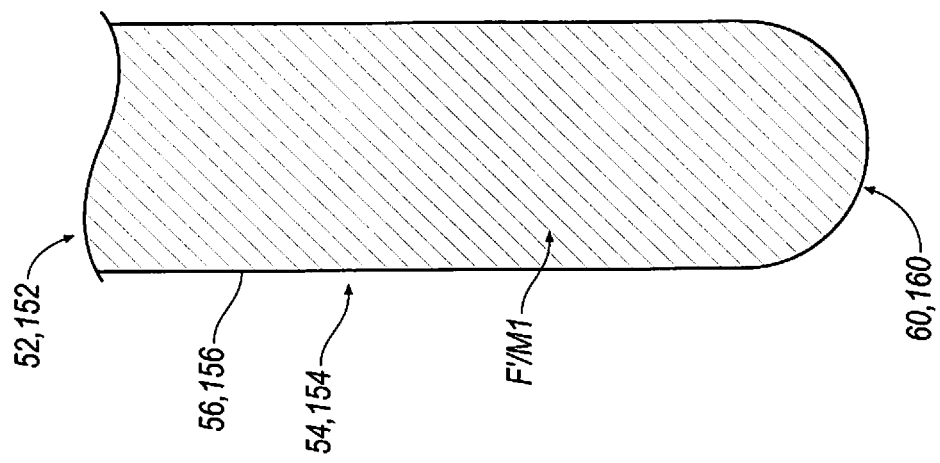

With reference to FIGS. 5A-5C, in some instances, the material defining the body 54, 154 of the sensor testing implement 52, 152 may include one material (e.g., a metallic material M1), or, alternatively, a combination of two or more materials (e.g., a metallic material M1 and a plastic material M2). In some examples, as seen for example in FIG. 5A, substantially all of the body 54, 154 of the sensor testing implement 52, 152 extending between the proximal end 58, 158 and the distal end 60, 160 may include one material M1 (e.g., a metallic material that functions as the non-foodstuff material F' to be detected by the foreign object sensor 18, 118). In other examples, as seen, for example, in FIGS. 5B and 5C, at least a portion of the body 54, 154 proximate the distal end 60, 160 of the sensor testing implement 52, 152 includes a first material M1 (e.g., a metallic material that functions as a non-foodstuff material F' to be detected by the foreign object sensor 18, 118) whereas the remainder of the body 54, 154 of sensor testing implement 52, 152 may include a second material M2 (e.g., a plastic material) that is not detectable by the foreign object sensor 18, 118.

Referring to FIG. 5B, in one example, the first material M1 of the exemplary sensor testing implement 52, 152 may be connected to the second material M2 by way of, for example, a mechanical connection, a friction-fit connection, or with an adhesive. As seen in FIG. 5B, a first portion of the first material M1 is exposed to surrounding atmosphere whereas a second portion of the first material M1 is disposed adjacent the second material M2, and, therefore, not exposed to surrounding atmosphere. In some examples, as seen in FIG. 5B, the first material M1 may be a metal ball or ball bearing that is secured to and received within a corresponding pocket or recess defined by the second material M2, which may be a plastic material.

Referring to FIG. 5C, in another example, the first material M1 of the exemplary sensor testing implement 52, 152 may be connected to the second material M2 by way of, for example, an over-molding connection. As seen in FIG. 5C, all of the first material M1 is encapsulated by the second material M2, and, therefore the first material M1 is not exposed to surrounding atmosphere. In some examples, as seen in FIG. 5C, the first material M1 may be a metal ball or ball bearing that is secured to and received within a corresponding pocket or recess defined by the second material M2, which may be a plastic material.

One or both of the first material M1 and the second material M2 may be a food-grade material. A metallic material M1 forming the sensor testing implement 52, 152 may be any type of food-grade metallic material such as, for example: stainless steel, aluminum, copper, carbonized metal, cast iron, galvanized iron, titanium, platinum or gold. A plastic material M2 forming the sensor testing implement 52, 152 may be any type of food-grade plastic material such as, for example: high density polyethylene (HDPE), low density polyethylene (LDPE), polypropylene (PP) or polyethylene terephthalate (PETE). Although one or both of the first material M1 and the second material M2 may be any type of food-grade material, the sensor testing implement 52, 152 (and system associated therewith) is not limited to use in the food manufacturing/processing industry. Therefore, in some examples, both of the first material M1 and the second material M2 may be any type of non-food-grade material, and, as such, the sensor testing implement 52, 152 (and system associated therewith) may be applied to any industry such as, for example: the soap production industry, the concrete production industry or the like.

As seen in FIGS. 4 and 6, the proximal end 58, 158 of the sensor testing implement 52, 152 may include a handle portion 78, 178. With reference to FIG. 6, the handle portion 78, 178 includes a body 80, 180. A passage 82, 182 may extend through the body 80, 180. The body 80, 180 is generally divided into a grip portion 84, 184 and a sensor testing conduit registration portion 86, 186.

The grip portion 84, 184 may include a serpentine surface 88, 188 that partially defines the passage 82, 182 extending through the body 80, 180 of the handle portion 78, 178. The serpentine surface 88, 188 may assist in registering a user's fingers about the grip portion 84, 184 when a user grips the handle portion 78, 178 with his/her hand.

Although the body 80, 180 includes a passage 82, 182 partially defined by serpentine surface 88, 188 that may assist in registering a user's fingers about the grip portion 84, 184 (which may infer a manual use of the sensor testing implement 52, 152 in association with the exemplary food processing system 10 of FIG. 1 described above), the body 80, 180 is not limited to a particular structure, and, therefore, may include any desirable configuration that may correspond to a connection configuration that may be suitable for connection with, for example the actuator 162 of the exemplary food processing system 100 of FIG. 2, which may, in some instances, operate in an automatic or automated manner.

The sensor testing conduit registration portion 86, 186 may include one or more surface portions 90, 92, 190, 192. The one or more surface portions 90, 92, 190, 192 may be deliberately shaped to mate with a corresponding surface geometry of the proximal end 42, 142 of the body 36, 136 of the sensor testing conduit 34, 134. In an example, the one or more surface portions 90, 92, 190, 192 defining the sensor testing conduit registration portion 86, 186 may include a first surface portion 90, 190 and a second surface portion 92, 192. The first surface portion 90, 190 and the second surface portion 92, 192 may angularly diverge from one another. In particular, in some configurations, the first surface portion 90, 190 and the second surface portion 92, 192 may define an angle θ1 therebetween. The angle θ1 may be approximately equal to 135°. In this regard, in some configurations the first surface portion 90, 190 and the second surface portion 92, 192 may define a generally frustoconical shape and/or configuration.

Figures 7, 8:
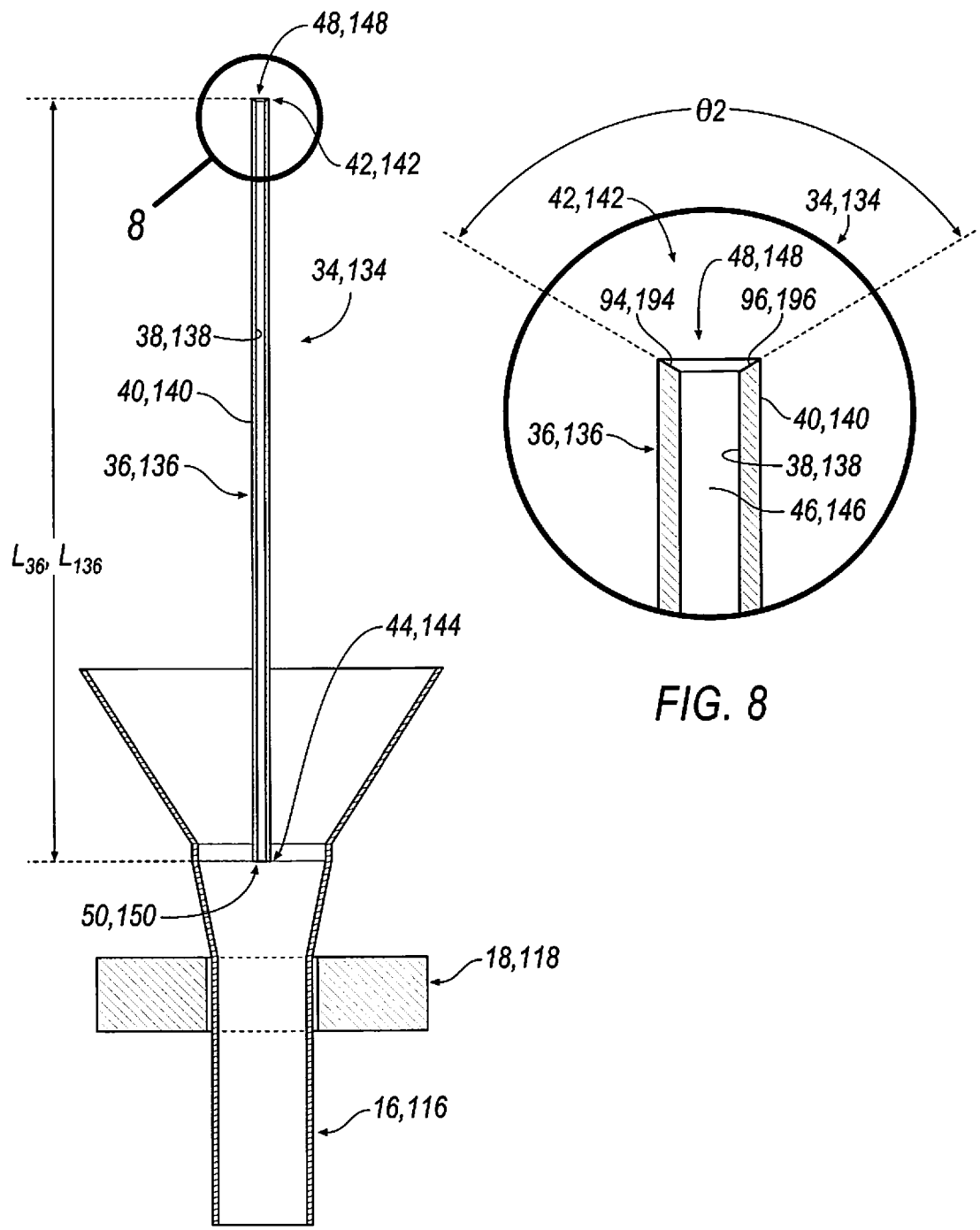
FIG. 7 is cross-sectional view of an exemplary portion of the food processing system of FIG. 1 or FIG. 2.
FIG. 8 is an enlarged view of a portion of the food processing system according to line 8 of FIG. 7.

Referring to FIGS. 7 and 8, an exemplary proximal end 42, 142 of the sensor testing conduit 34, 134 is shown, which also includes: the entrance opening 48, 148, a portion of the inner surface 38, 138, a portion of the outer surface 40, 140 and a portion of the passage 46, 146 extending through the body 36, 136 from the proximal end 42, 142. As seen in FIG. 8, the inner surface 38, 138 includes one or more surface portions 94, 96, 194, 196 proximate the entrance opening 48, 148 of the sensor testing conduit 34, 134. The surface portions 94, 96, 194, 196 may extend from the outer surface 40, 140 to the inner surface 38, 138. In some configurations, the surface portions 94, 96, 194, and/or 196 may be flared and/or chamfered. In this regard, as illustrated, the chamfered surface portions 94, 96, 194, 196 may define a portion of the inner surface 38, 138 of the sensor testing conduit 34, 134. The one or more surface portions 94, 96, 194, 196 may be deliberately shaped to mate with a corresponding surface geometry of the one or more surface portions 90, 92, 190, 192 of the sensor testing conduit registration portion 86, 186 of the body 80, 180 of the handle portion 78, 178 of the proximal end 58, 158 of the sensor testing implement 52, 152.

In an example, the one or more surface portions 94, 96, 194, 196 extending from the inner surface 38, 138 proximate the proximal end 42, 142 of the sensor testing conduit 34, 134 may include a first chamfered surface portion 94, 194 and a second chamfered surface portion 96, 196. In some configurations the chamfered surface portion 94, 194 may extend from and between the chamfered surface portion 96, 196. For example, the chamfered surface portion 94, 194 and the chamfered surface portion 96, 196 may define an annular inner periphery proximate the entrance opening 48, 148. The first chamfered surface portion 94, 194 and the second chamfered surface portion 96, 196 may define an angle θ2 therebetween. The angle θ2 may be between 180° and 275°. In some configurations, the angle θ2 which may be approximately equal to 225°. In particular, the angle θ2 may be substantially equal to (+/−5°) the angle θ1.

Figure 9:
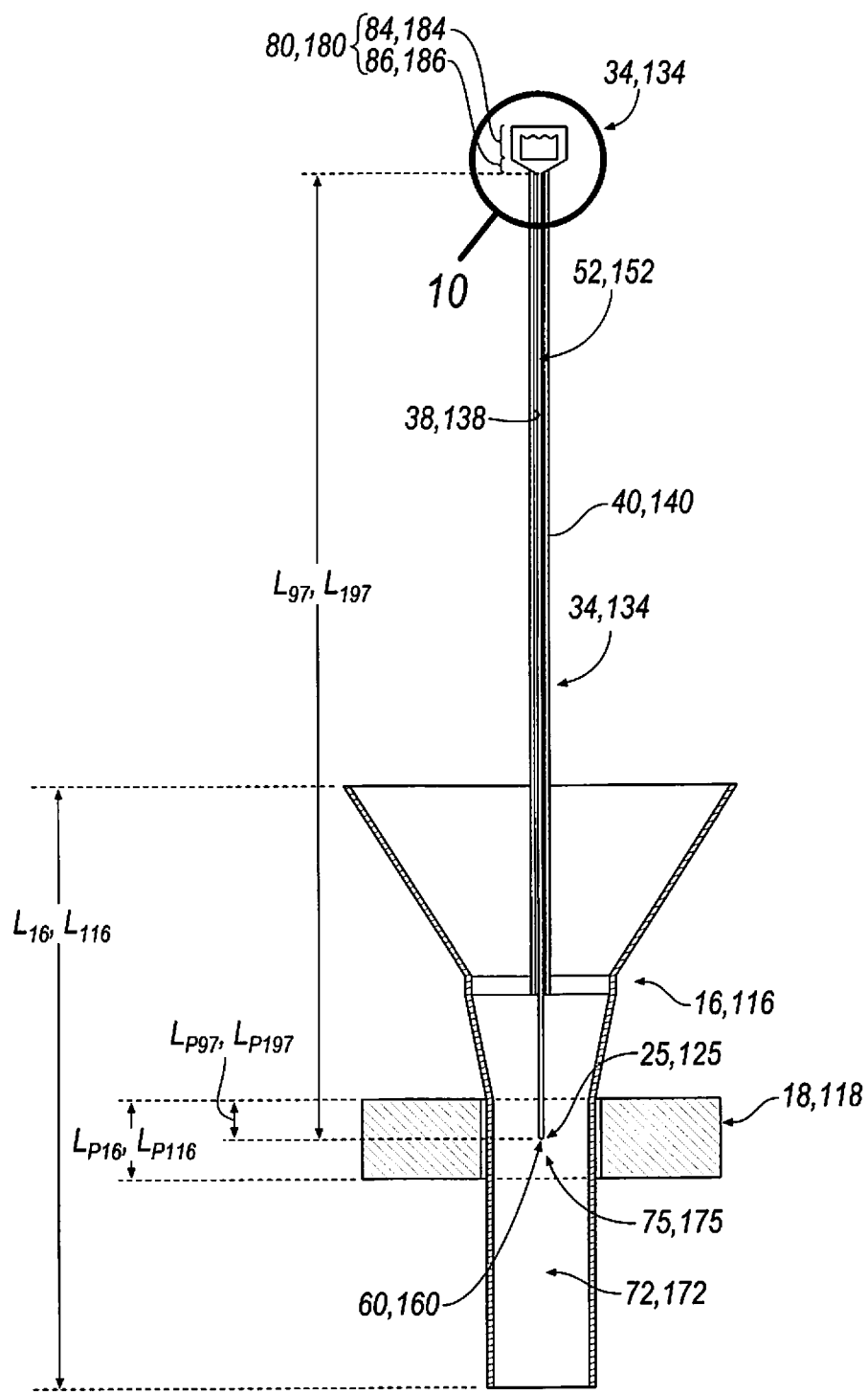
FIGS. 9 and 9B are views of the sensor testing implement of FIG. 6 interfaced with the portion of the food processing system of FIG. 7.
Figure 10:
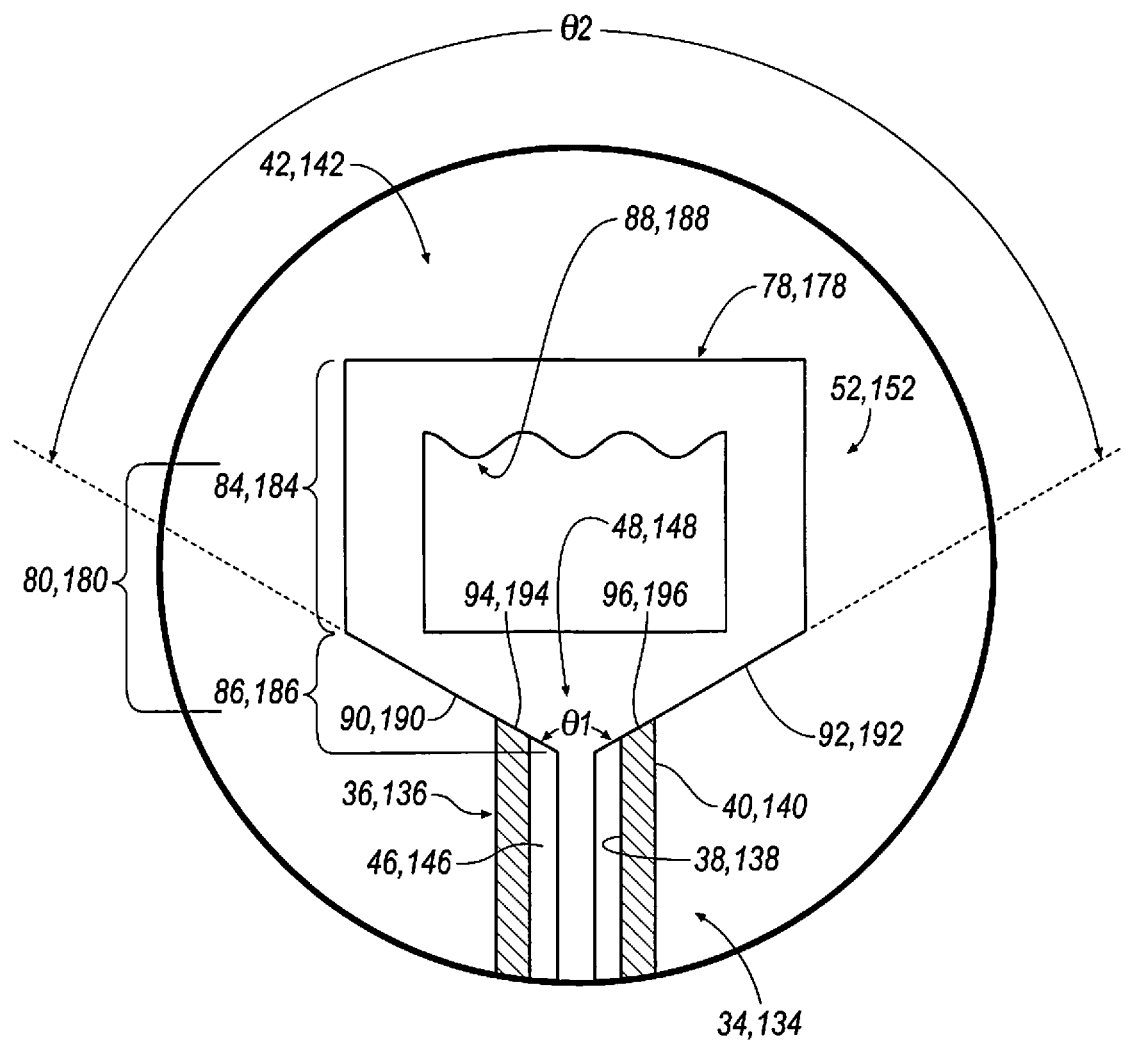
FIG. 10 is an enlarged view according to line 10 of FIG. 9.

Referring to FIGS. 9 and 10, the sensor testing implement 52, 152 may be consistently and repeatably arranged in a fully deployed orientation when the sensor testing conduit registration portion 86, 186 is registered within the entrance opening 48, 148 of the sensor testing conduit 34, 134. As seen in FIG. 10, at least a portion of the first surface portion 90, 190 and at least a portion of the second surface portion 92, 192 of the sensor testing implement 52, 152 may be matingly-received by and disposed adjacent the first surface portion 94, 194 and the second surface portion 96, 196 proximate the entrance opening 48, 148 of the sensor testing conduit 34, 134. In addition to providing the ability to consistently and repeatably arrange the sensor testing implement 52, 152 in a fully deployed orientation, some of the first surface portion 90, 190 and some of the second surface portion 92, 192 of the sensor testing implement 52, 152 may laterally and/or radially extend beyond the outer surface 40, 140 of the body 36, 136 of the sensor testing conduit 34, 134 in order to prevent further plunging of the sensor testing implement 52, 152 through the entrance opening 48, 148 of the sensor testing conduit 34, 134 once at least a portion of the first surface portion 90, 190 and at least a portion of the second surface portion 92, 192 of the sensor testing implement 52, 152 are matingly-received by and disposed adjacent the first surface portion 94, 194 and the second surface portion 96, 196 of the sensor testing conduit 34, 134. In this regard, the surface portions 90, 190, 92, 192 of the sensor testing implement 52, 152 may mate with the surface portions 94, 194, 96, 196 of the sensor testing conduit 34, 134 to collectively define a stop and prevent translation of, and/or relative movement between, the sensor testing implement 52, 152 and the sensor testing conduit 34, 134 in one or more directions.

Referring to FIG. 4, the sensor testing implement 52, 152 may include a shaft portion 97, 197. The shaft portion 97, 197 includes a proximal end 98, 198 connected to the first surface portion 90, 190 and the second surface portion 92, 192 of the handle portion 78, 178 of the sensor testing implement 52, 152. The distal end 60, 160 of the sensor testing implement 52, 152 may also include the distal end of the shaft portion 97, 197. The shaft portion 97, 197 is defined by a length $L_{97}$, $L_{197}$ extending between the proximal end 98, 198 of the shaft portion 97, 197 and the distal end 60, 160 of the shaft portion 97, 197.

With reference to FIG. 9, a portion of the passage 72, 172 extending through the chute portion 16, 116 may define a foreign object sensing zone 25, 125. The foreign object sensing zone 25, 125 may be axially bound by a portion $L_{P16}$, $L_{P116}$ of a length $L_{16}$, $L_{116}$ of the body 66, 166 of the chute portion 16, 116. The portion $L_{P16}$, $L_{P116}$ of a length $L_{16}$, $L_{116}$ of the body 66, 166 of the chute portion 16, 116 is defined by an arrangement of the foreign object sensor 18, 118 relative the chute portion 16, 116. For example, the foreign object sensor 18, 118 may be aligned with and/or otherwise define at least a portion of the foreign object sensing zone 25, 125. In particular, an axially extending length of the foreign object sensor 18, 118 may be substantially equal to (+/−15%) the axially extending length of the foreign object sensing zone 25, 125. In this regard, the axially extending length of the foreign object sensor 18, 118 and the axially extending length of the foreign object sensing zone 25, 125 may be substantially equal to (+/−15%) the axially extending length of the portion $L_{P16}$, $L_{P116}$ of a length $L_{16}$, $L_{116}$ of the body 66, 166 of the chute portion 16, 116. A spatial center of the foreign object sensing zone 25, 125 is seen at reference numeral 75, 175.

The length $L_{97}$, $L_{197}$ of the shaft portion 97, 197 of the sensor testing implement 52, 152 may be selectively-sized such that when the sensor testing implement 52, 152 is arranged in a fully deployed orientation, the distal end 60, 160 of the shaft portion 97, 197 may be spatially arranged in the spatial center 75, 175 of the foreign object sensing zone 25, 125. As such, if, for example, at least a portion of the distal end 60, 160 of the sensor testing implement 52, 152 includes the first material M1 (e.g., a metallic material) that functions as a non-foodstuff material F' to be detected by the foreign object sensor 18, 118, the ability for the sensor testing implement 52, 152 to be consistently repeatably arranged in a fully deployed orientation (as a result of the sensor testing conduit registration portion 86, 186 being registered within the entrance opening 48, 148 of the sensor testing conduit 34, 134 as described above) ensures that the distal end 60, 160 of the sensor testing implement 52, 152 including the first material M1 (e.g., a metallic material) may be consistently repeatably arranged within the spatial center 75, 175 of the foreign object sensing zone 25, 125.

In other examples, the length $L_{97}$, $L_{197}$ of the shaft portion 97, 197 may be selectively-sized such that when the sensor testing implement 52, 152 is arranged in a fully deployed orientation, a portion $L_{P97}$, $L_{P197}$ (see FIGS. 4 and 9) of the length $L_{97}$, $L_{197}$ of the shaft portion 97, 197 extending away from the distal end 60, 160 of the shaft portion 97, 197 may be spatially arranged in the foreign object sensing zone 25, 125. As such, if, for example, the portion $L_{P97}$, $L_{P197}$ (see FIGS. 4 and 9) of the length $L_{97}$, $L_{197}$ of the shaft portion 97, 197 extending away from the distal end 60, 160 of the shaft portion 97, 197 of the sensor testing implement 52, 152 includes the first material M1 (e.g., a metallic material) that functions as a non-foodstuff material F' to be detected by the foreign object sensor 18, 118, the ability for the sensor testing implement 52, 152 to be consistently repeatably arranged in a fully deployed orientation (as a result of the sensor testing conduit registration portion 86, 186 being registered within the entrance opening 48, 148 of the sensor testing conduit 34, 134 as described above) ensures that the portion $L_{P97}$, $L_{P197}$ of the length $L_{97}$, $L_{197}$ of the shaft portion 97, 197 extending away from the distal end 60, 160 of the shaft portion 97, 197 of the sensor testing implement 52, 152 including the first material M1 (e.g., a metallic material) may be consistently repeatably arranged within the foreign object sensing zone 25, 125.

Figure 9A:
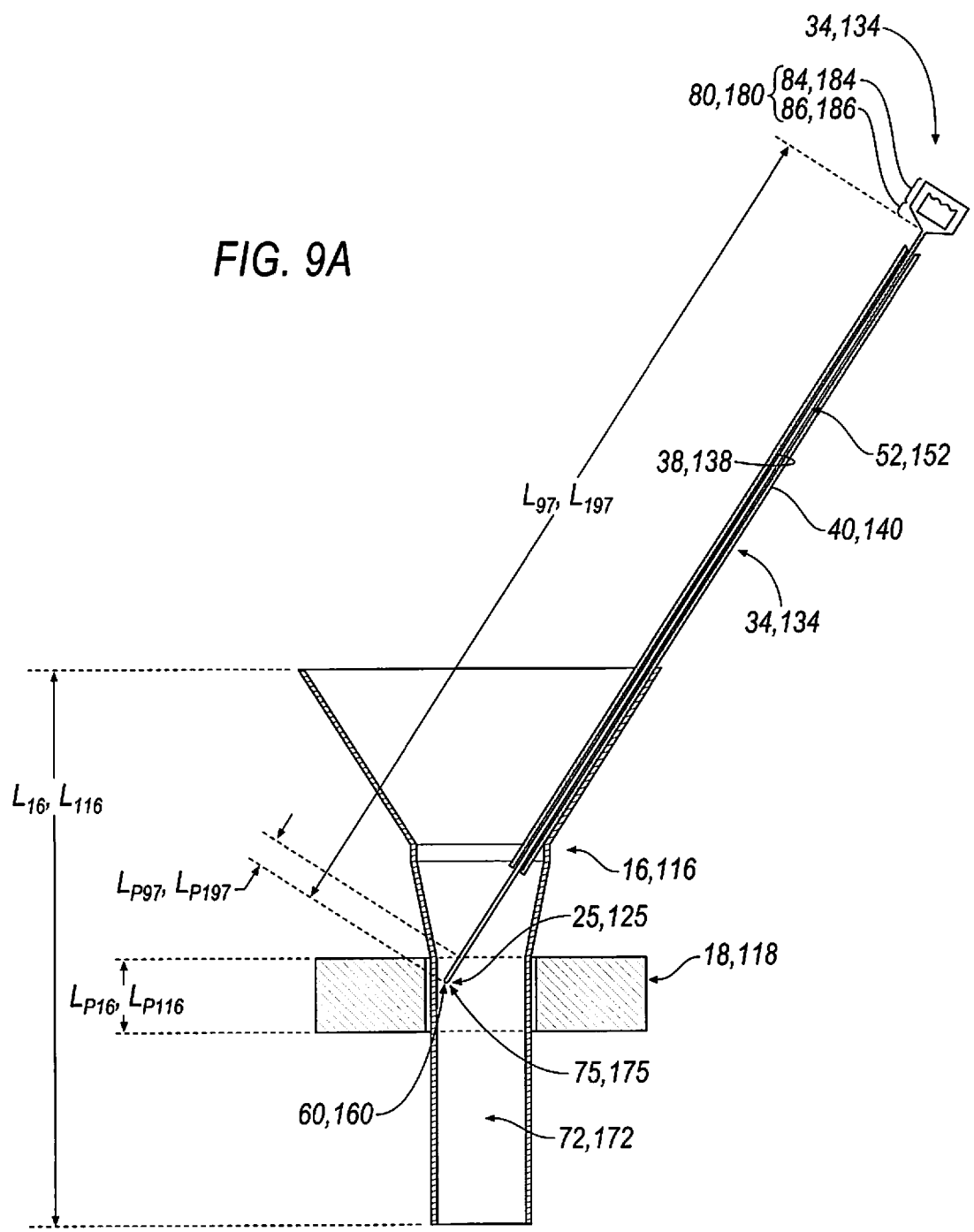
Figure 9B:
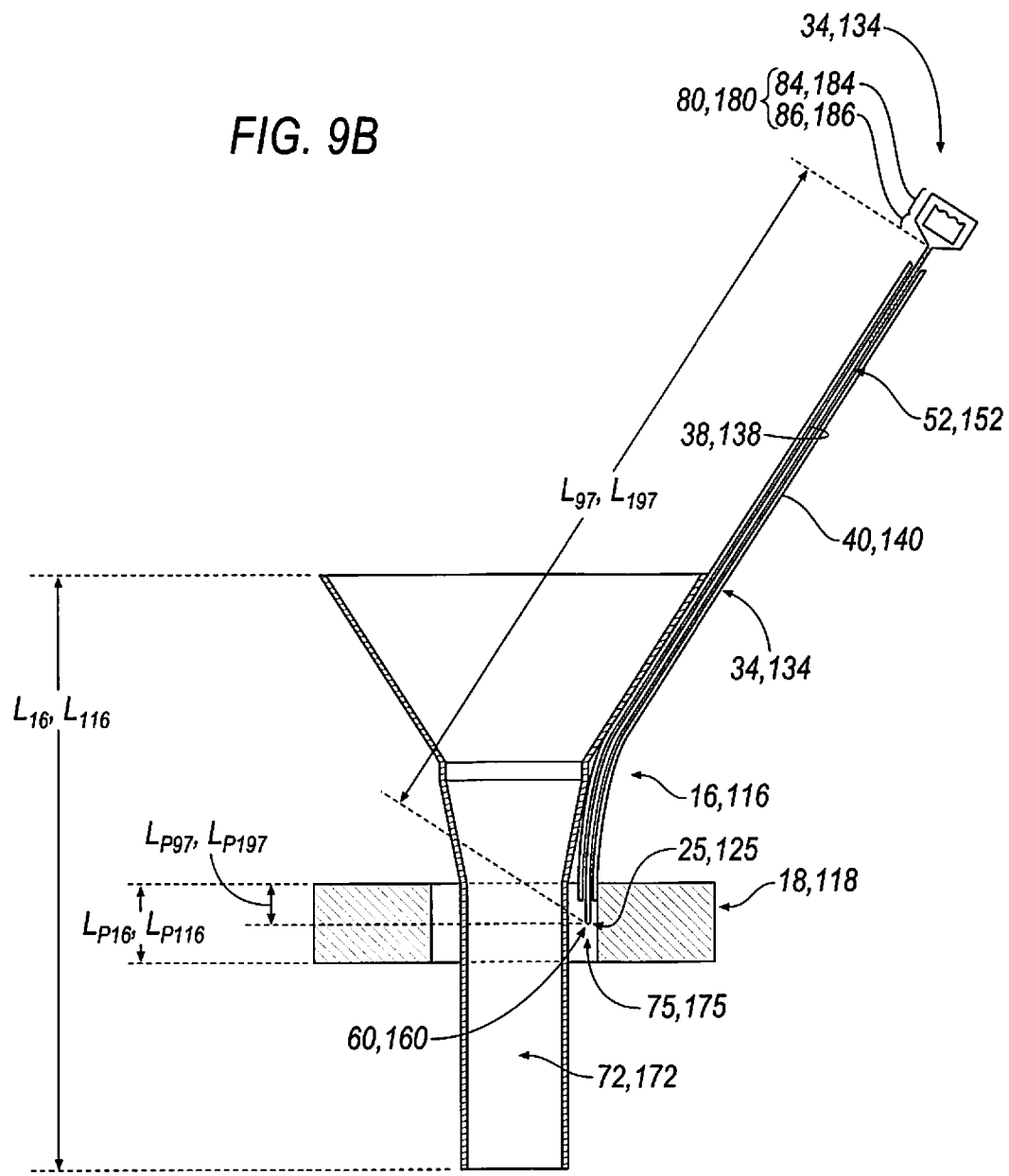

With continued reference to FIG. 9, some implementations of the arrangement of the sensor testing conduit 34, 134 relative the chute portion 16, 116 may result in the sensor testing conduit 34, 134 being axially aligned with an axial center of a portion of the passage 72, 172 extending through the chute portion 16, 116. As such, the distal end 60, 160 of the shaft portion 97, 197 may be not only be spatially arranged in the spatial center 75, 175 of the foreign object sensing zone 25, 125 but also in the axial center of the foreign object sensing zone 25, 125. Although some arrangements of the sensor testing conduit 34, 134 relative the chute portion 16, 116 may result in the sensor testing conduit 34, 134 being axially aligned with an axial center of a portion of the passage 72, 172 extending through the chute portion 16, 116 as described above, other implementations of the sensor testing conduit 34, 134 relative the chute portion 16, 116 may include non-axially-aligned arrangements of the sensor testing conduit 34, 134 relative the chute portion 16, 116. For example, as seen in FIG. 9A, the sensor testing conduit 34, 134 may be disposed within a portion of the passage 72, 172 extending through the chute portion 16, 116 in a manner that is offset from an axial center of the passage 72, 172 extending through the chute portion 16, 116 (e.g., as seen in FIG. 9A, the sensor testing conduit 34, 134 may be disposed adjacent the inner surface 68, 168 of the body 66, 166 of the chute portion 16, 116). In another example, as seen in FIG. 9B, the sensor testing conduit 34, 134 may be disposed exterior of the passage 72, 172 extending through the chute portion 16, 116 in a manner that is not axially aligned with an axial center of the passage 72, 172 extending through the chute portion 16, 116 (e.g., as seen in FIG. 9B, the sensor testing conduit 34, 134 may be disposed adjacent the outer surface 70, 170 of the body 66, 166 of the chute portion 16, 116). Although the sensor testing conduit 34, 134 is not axially aligned with an axial center of the passage 72, 172 extending through the chute portion 16, 116 of the exemplary implementations described above at FIGS. 9A-9B, the sensor testing conduit 34, 134 is arranged relative the chute portion 16, 116 such that the distal end 60, 160 of the shaft portion 97, 197 of the sensor testing implement 52, 152 traverses the foreign object sensing zone 25, 125.

Figure 4A:
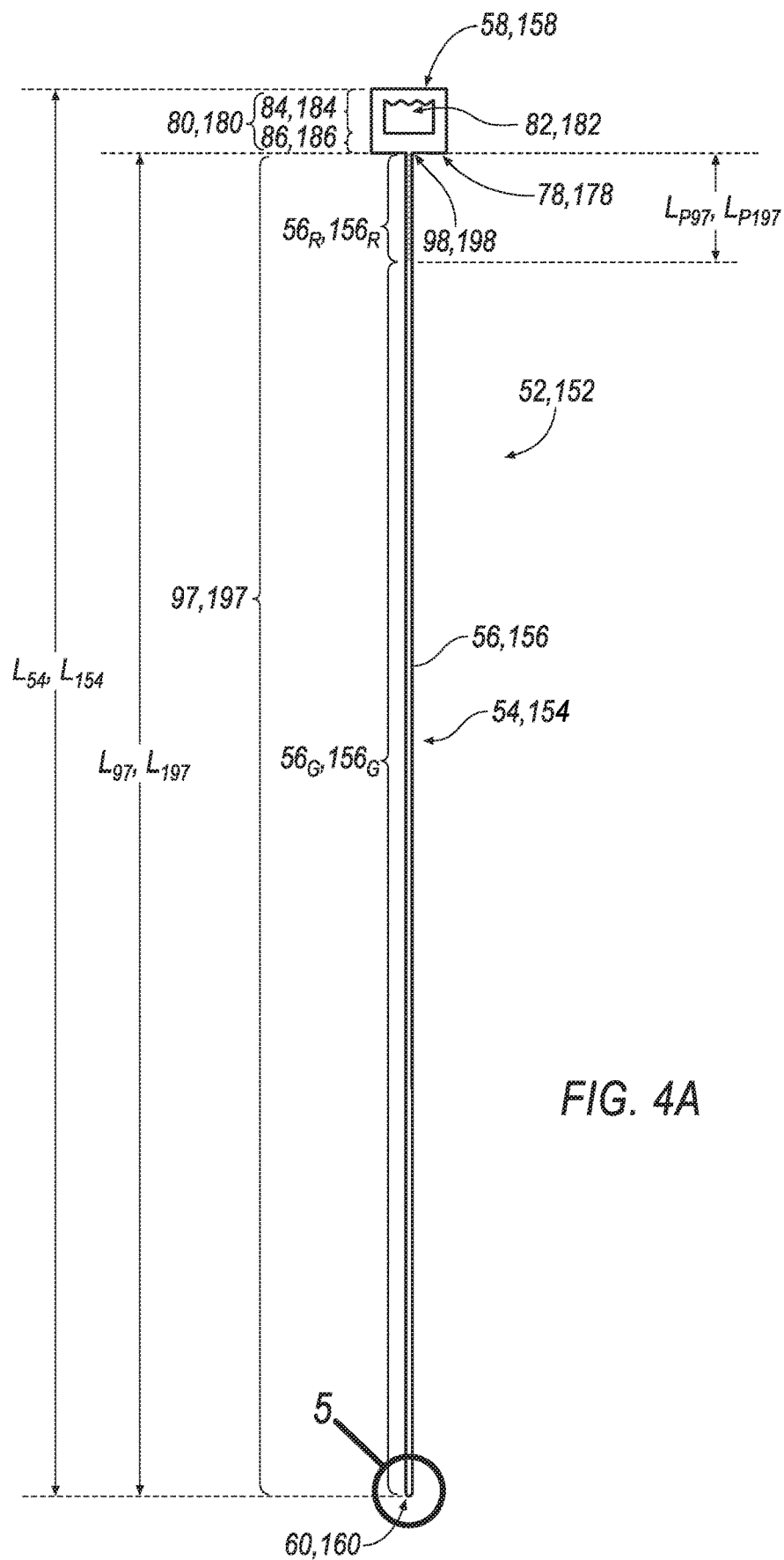

Furthermore, although the provision of a physical stop provided with the sensor testing implement 52, 152 has been described above at FIGS. 4, 6 and 9, for the purpose of automatically repeatably-controlling positioning of the sensor testing implement 52, 152 relative the sensor testing conduit 34, 134 such that the sensor testing implement 52, 152 is sufficiently inserted into the entrance opening 48, 148 of the sensor testing conduit 34, 134 for permitting the distal end 60, 160 of the sensor testing implement 52, 152 to encounter the foreign object sensing zone 25, 125, other implementations of the sensor testing implement 52, 152 (that may or may not include the physical stop structure) may include, for example: letters, numbers, characters or a color-coding scheme (see, e.g., $56_G$, $56_R$; $156_G$, $156_R$ in FIG. 4A) provided on the outer surface 56, 156 of the sensor testing implement 52, 152. In an example, as seen in FIG. 4A, a color-coding scheme may provide a visual indicator to a user that assists the user in asserting independent control over the plunging movement of the sensor testing implement 52, 152 relative the entrance opening 48, 148 of the sensor testing conduit 34, 134. For example, a portion $56_G$, $156_G$ of the outer surface 56, 156 of the sensor testing implement 52, 152 proximate to and extending away from the distal end 60, 160 of the sensor testing implement 52, 152 may include, for example, a green coloring that provides a visual indicator communicating to a user that the sensor testing implement 52, 152 should be further plunged through the entrance opening 48, 148 of the sensor testing conduit 34, 134 whereas another portion $56_R$, $156_R$ of the outer surface 56, 156 of the sensor testing implement 52, 152 proximate to and extending away from the handle portion 78, 178 may include, for example, a red coloring that provides a visual indicator communicating to the user that further plunging of the sensor testing implement 52, 152 through the entrance opening 48, 148 of the sensor testing conduit 34, 134 may be selectively ceased (i.e., plunging of the sensor testing implement 52, 152 may be ceased at any time when any portion of the portion $56_R$, $156_R$ of the outer surface 56, 156 of the sensor testing implement 52, 152 is arranged within the entrance opening 48, 148 of the sensor testing conduit 34, 134 because the sensor testing implement 52, 152 has been sufficiently inserted into the entrance opening 48, 148 of the sensor testing conduit 34, 134 such that the foreign object sensor 18, 118 senses non-foodstuff material F' disposed within the distal end 60, 160 of the sensor testing implement 52, 152). In some instances, the portion $56_R$, $156_R$ of the outer surface 56, 156 of the sensor testing implement 52, 152 including, for example, red coloring provided by the outer surface 56, 156 of the sensor testing implement 52, 152 may extend away from the handle portion 78, 178 at a distance approximately equal to the portion $L_{P97}$, $L_{P197}$ of the length $L_{97}$, $L_{197}$ of the shaft portion 97, 197 (as similarly described above) in order to ensure that the foreign object sensor 18, 118 senses the distal end 60, 160 of the sensor testing implement 52, 152 containing the non-foodstuff material F'.

Figure 11A:
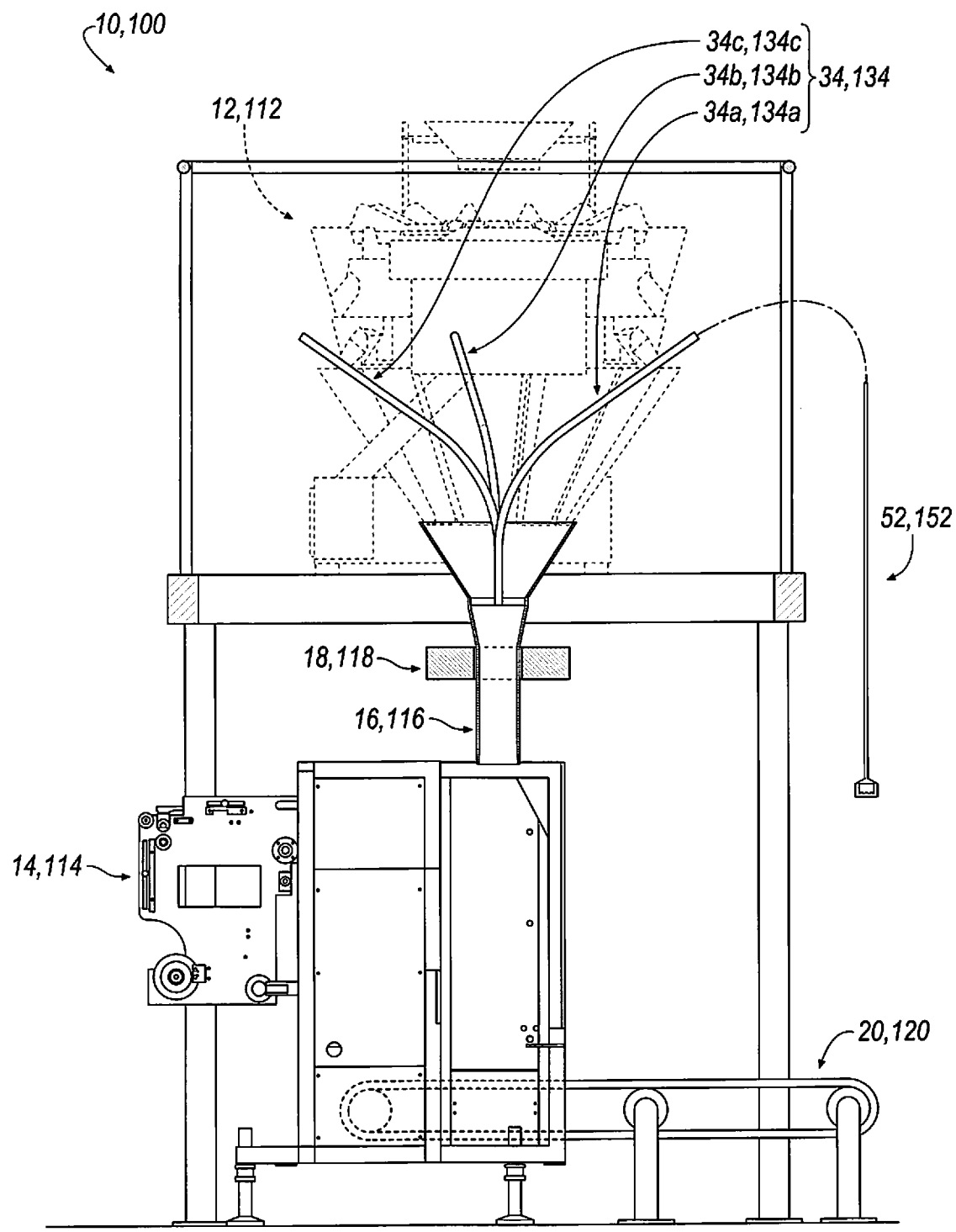
FIG. 11A is a side, partial cross-sectional view of a portion of the food processing system of FIG. 1 or FIG. 2 illustrating the sensor testing implement arranged in a retracted orientation.
Figure 11B:
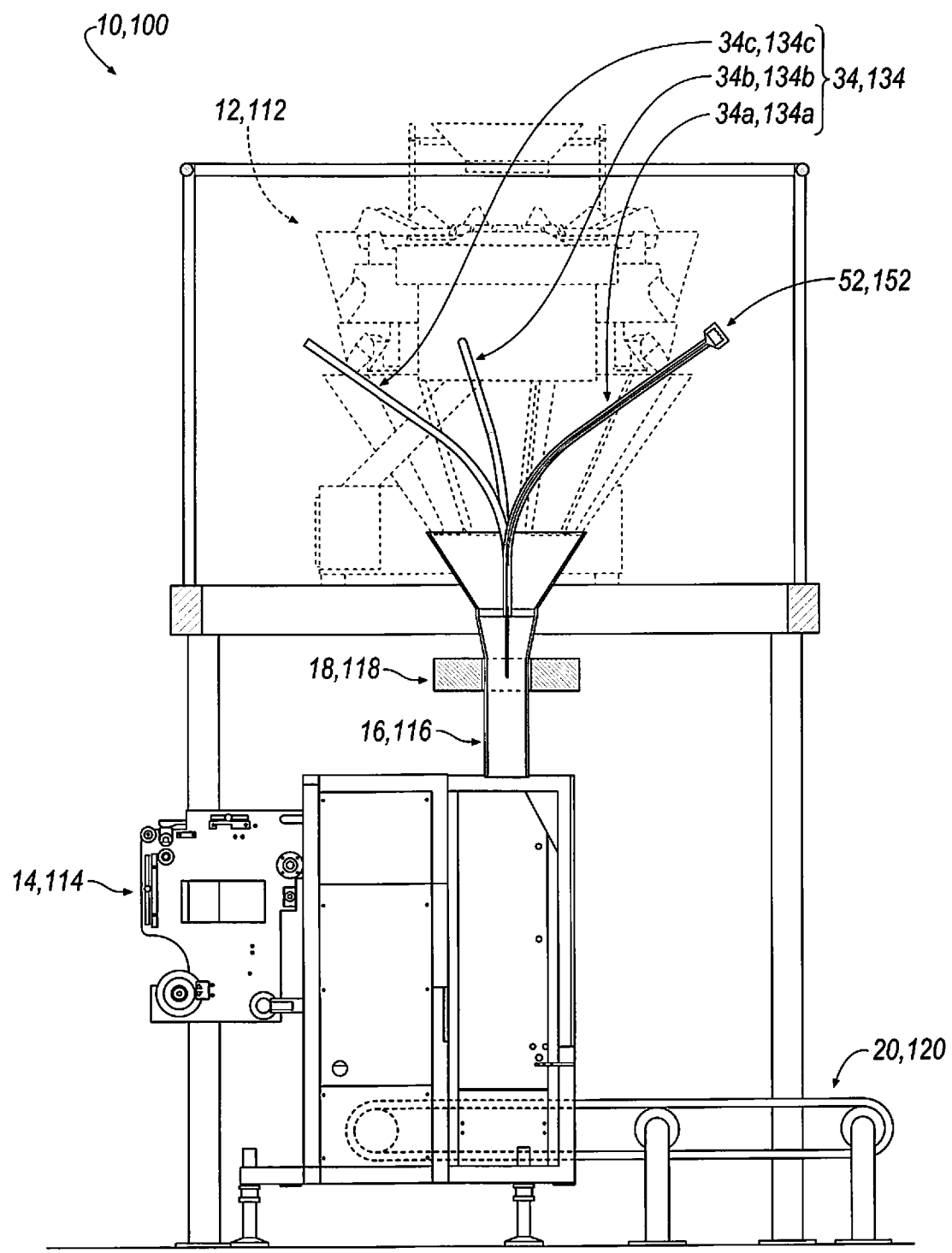
FIG. 11B is a side, partial cross-sectional view of a portion of the food processing system of FIG. 1 or FIG. 2 illustrating the sensor testing implement arranged in a deployed orientation.

Referring to FIGS. 11A and 11B, partial views of the structure forming the exemplary food processing systems 10, 100 are shown. The exemplary food processing system 10, 100 may include the components and features described above at reference numerals 12-98 and 112-198, and, therefore are not described in further detail here. The exemplary food processing systems shown at FIGS. 11A and 11B may include, however, one or more of the sensor testing conduits 34, 134 extending through both of the food scaling portion 12, 112 and the chute portion 16, 116. Furthermore, the sensor testing conduit(s) 34, 134 may be connected to one or both of the food scaling portion 12, 112 and the chute portion 16, 116.

As seen in FIGS. 11 A and 11B, the sensor testing conduit(s) 34, 134 may include a first sensor testing conduit 34a, 134a, a second sensor testing conduit 34b, 134b and a third sensor testing conduit 34c, 134c. Although three sensor testing conduits 34a, 34b, 34c, 134a, 134b, 134c are shown, the plurality of sensor testing conduits 34, 134 are not limited to including three sensor testing conduits. In some examples, the food scaling portion 12, 112 may include a plurality of food scaling channels whereby each channel of the plurality of food scaling channels guides a predetermined amount of foodstuff material F into the chute portion 16, 116. Therefore, in some instances, each channel of the plurality of food scaling channels may include a corresponding sensor testing conduit 34, 134.

If the exemplary food processing system 10 of FIGS. 11A and 11B is manually operated, the exemplary food processing system 10 may permit the sensor testing implement 52 to be interfacably-disposed within any of the one or more sensor testing conduit(s) 34. However, if desired, the exemplary food processing system 10 of FIGS. 11A and 11B may include more than one sensor testing implement 52. For example, in some instances, each sensor testing conduit 34a-34c of the plurality of sensor testing conduits 34 may include a corresponding sensor testing implement 52, 152 removably-disposable therein.

In another example, if the exemplary food processing system 100 of FIGS. 11A and 11B is automatically and/or manually operated, the exemplary food processing system 100 may also include a plurality of sensor testing implements 152 (even though only one sensor testing implement 152 is shown). In such a configuration, the exemplary food processing system 100 of FIGS. 11A and 11B may include a sensor testing implement 152 removably-disposable within each sensor testing conduit 134a-134c of the plurality of sensor testing conduits 134.

Figure 12A:
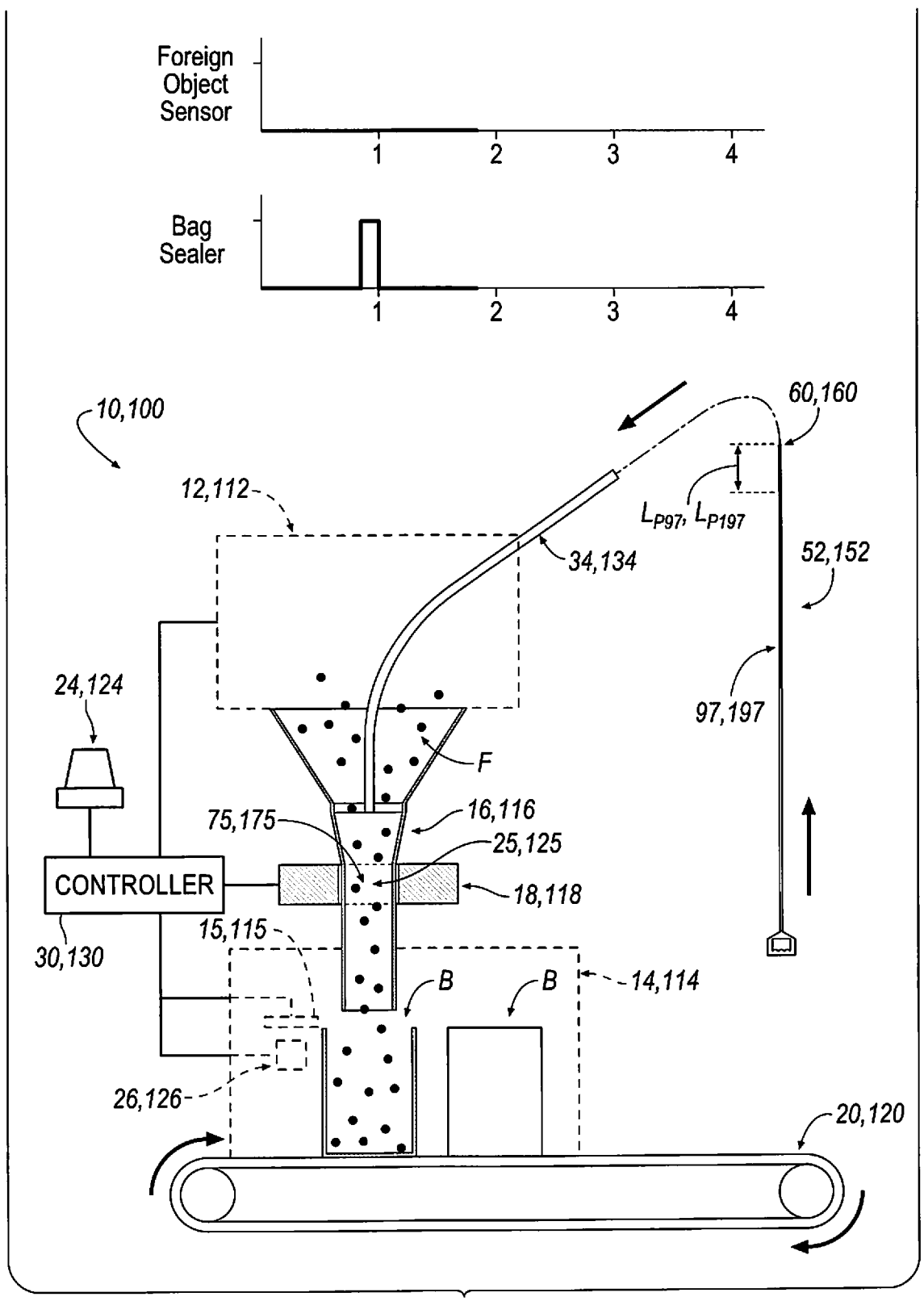
FIG. 12A is a side, partial cross-sectional view of a portion of the food processing system of FIG. 1 or FIG. 2 illustrating the sensor testing implement arranged in a retracted orientation.
Figure 12B:
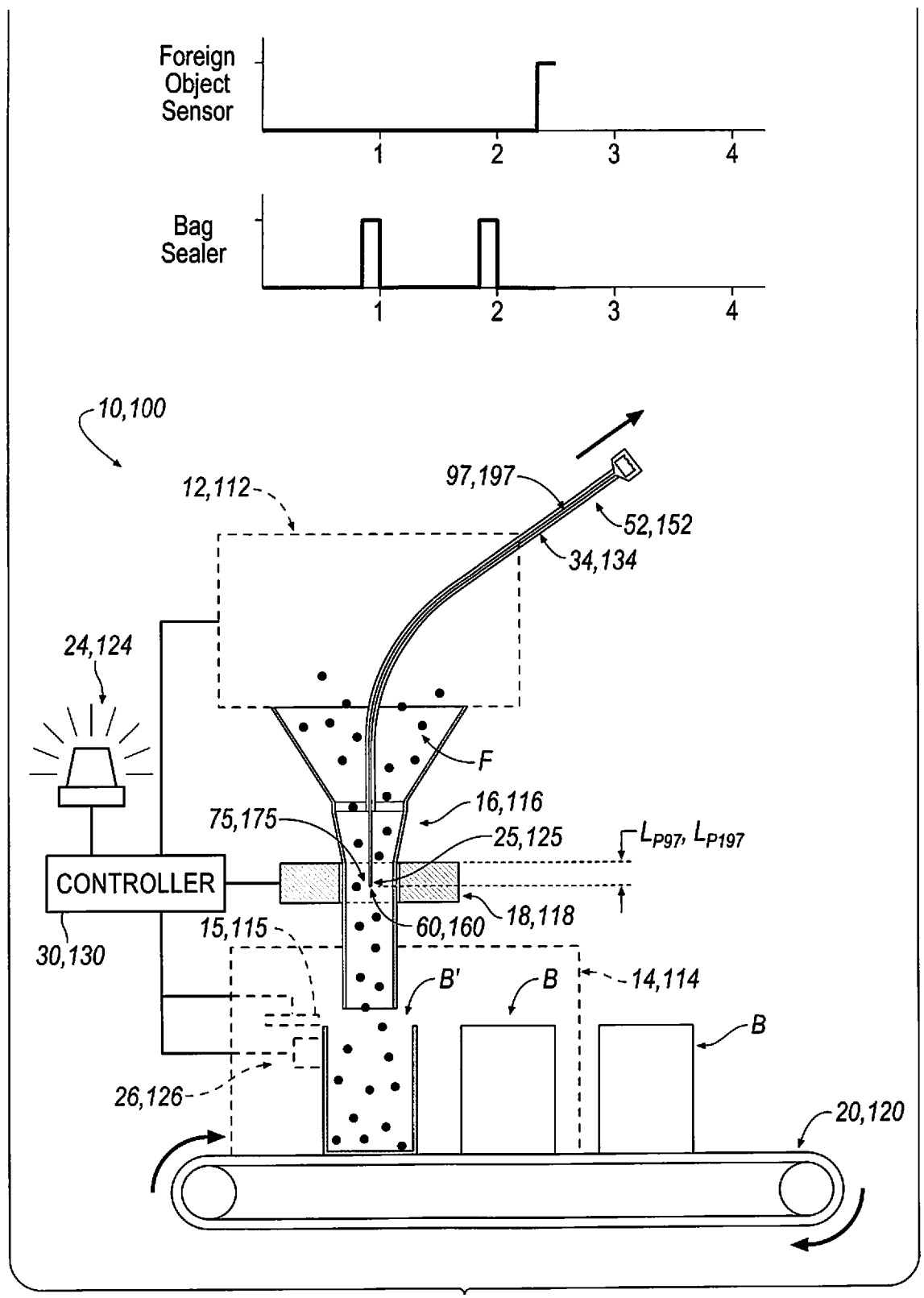
FIG. 12B is a side, partial cross-sectional view of a portion of the food processing system of FIG. 1 or FIG. 2 illustrating the sensor testing implement arranged in a deployed orientation.
Figure 12C:
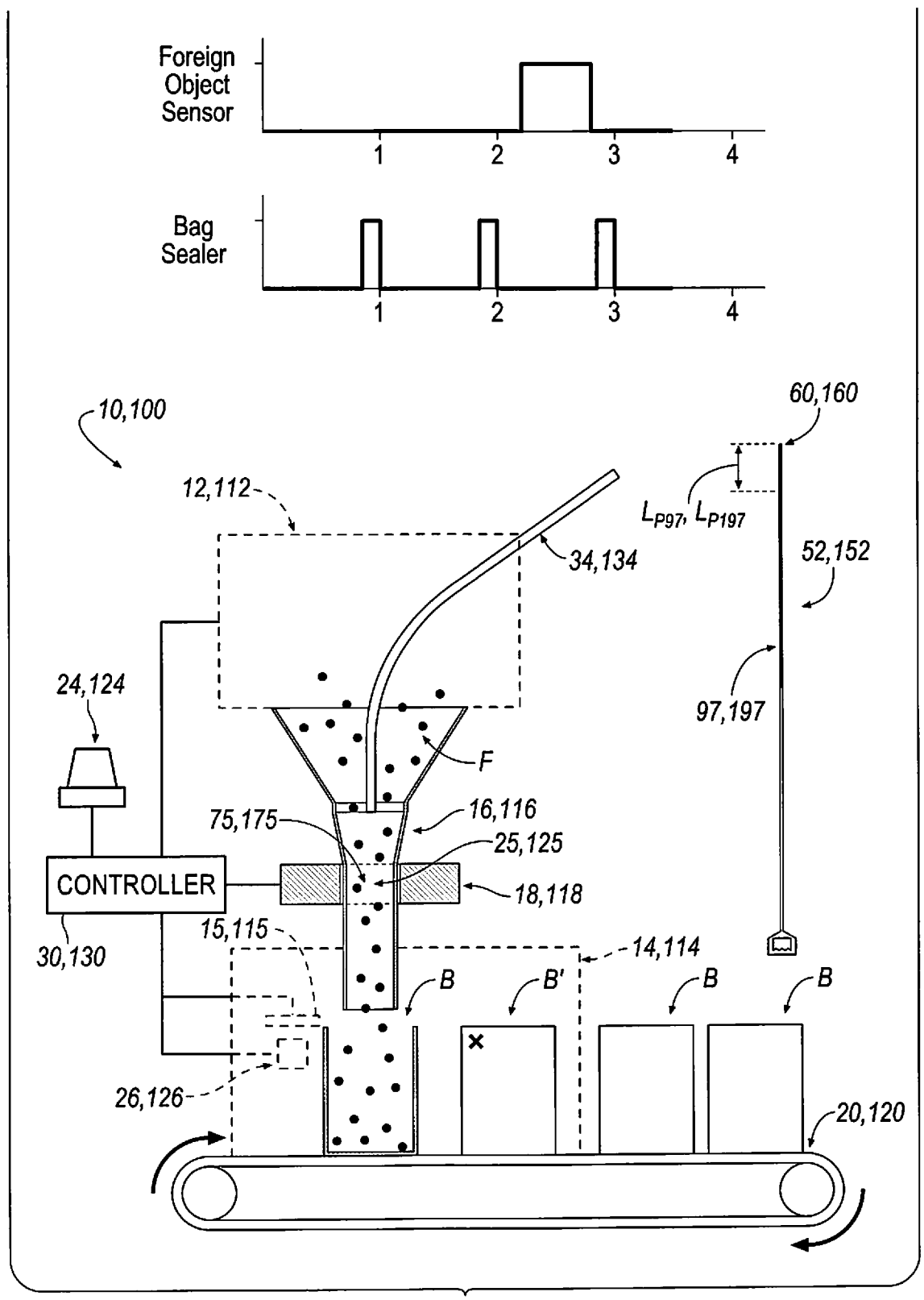
FIG. 12C is a side, partial cross-sectional view of a portion of the food processing system of FIG. 1 or FIG. 2 illustrating the sensor testing implement returned to the retracted orientation.

Referring to FIGS. 12A-12C, an exemplary methodology (see also 200 in FIG. 15) for operating either of the food processing systems 10, 100 is shown. Firstly, the food bagging portion 14, 114 may form a bag B having a sealed lower end and an open, non-sealed, upper end (see step 201 in FIG. 15). The scaling portion 12, 112 meters a desired amount of foodstuff material F that is subsequently received at the food bagging portion 14, 114 (see step 202 in FIG. 15). The chute portion 16, 116 guides the metered amount of the foodstuff material F from the scaling portion 12, 112 to the food bagging portion 14, 114 (see step 203 in FIG. 15).

The open, non-sealed upper end of the bag B receives the metered amount of foodstuff material F from the chute portion 16, 116. Once the metered amount of foodstuff material F is disposed within the bag, the bag B may be said to be filled with the foodstuff material F (see step 204 in FIG. 15). The controller 30, 130 may actuate a sealer 15, 115 of the food bagging portion 14, 114 for sealing and therefore closing the open, non-sealed upper end of the bag B (see step 206a in FIG. 15). The controller 30, 130 may also actuate the conveyor portion 20, 120 for shuttling the formed, filled and sealed bag B away from the food bagging portion 14, 114 (see step 207a in FIG. 15). For example, after the upper end of the bag B is sealed, the controller 30, 130 may actuate the conveyor portion 20, 120 for shuttling the formed, filled and sealed bag B away from the food bagging portion 14, 114. After shuttling the formed, filled, and sealed bag B away from the food bagging portion 14, 114, the food bagging portion 14, 114 may form another bag B having a sealed lower end and an open, non-sealed, upper end and repeat the above-described steps in a looped manner.

Figure 15:
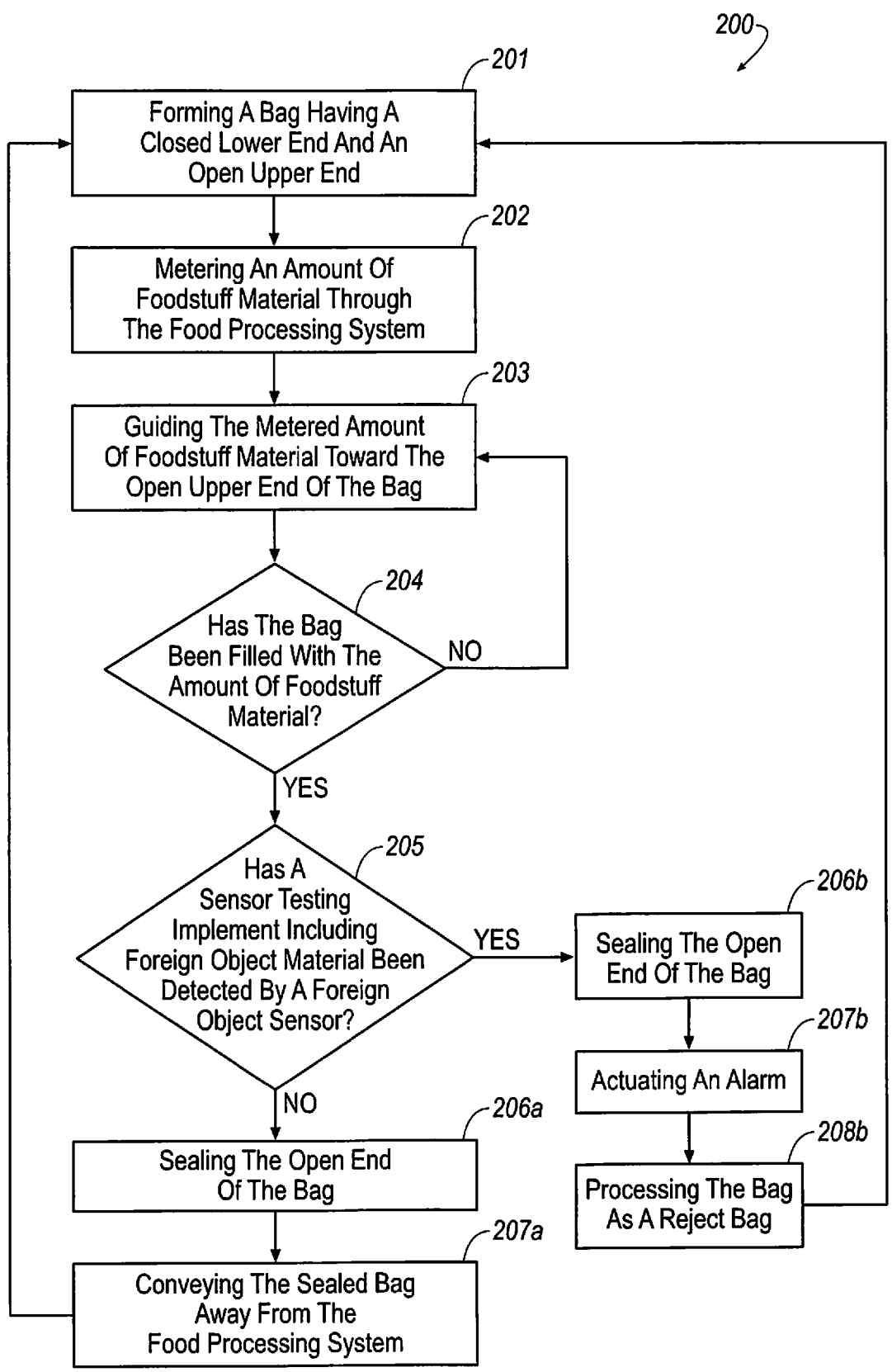
FIG. 15 is a method diagram associated with the food processing system of FIG. 1 or FIG. 2.

Referring to FIGS. 12A-12B, at any time during the operation of the food processing system 10, 100, the sensor testing implement 52, 152 may be plunged into the sensor testing conduit 34, 134 (see step 205 in FIG. 15). For example, the sensor testing implement 52, 152 may be plunged into the sensor testing conduit 34, 134 such that: (1) the distal end 60, 160 of the shaft portion 97, 197 may be spatially arranged substantially in the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 may be spatially arranged in the foreign object sensing zone 25, 125. For example, the distal end 60, 160 of the shaft portion 97, 197 and/or the portion $L_{P97}$, $L_{P197}$ of the length $L_{97}$, $L_{197}$ of the shaft portion 97, 197 may be axially aligned with the spatial center 75, 175 of the foreign object sensing zone 25, 125, such that the foreign object sensor 18, 118 can be purposefully actuated and/or detect the presence of the first material M1 of the sensor testing implement 52, 152. Then, as seen in FIGS. 12B-12C, at any time during the operation of the food processing system 10, 100, the sensor testing implement 52, 152 may be at least partially retracted from the sensor testing conduit 34, 134 such that: (1) the distal end 60, 160 of the shaft portion 97, 197 may not be spatially arranged substantially in the spatial center 75, 175 of the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 is not spatially arranged in the foreign object sensing zone 25, 125.

As seen in FIGS. 12A-12C, corresponding exemplary views of signal diagrams communicated to and/or processed by the controller 30, 130 are shown for the foreign object sensor 18, 118 and the bag sealer 15, 115. A low signal from the bag sealer 15, 115 may correspond to filling a formed bag B with foodstuff material F (see step 204 in FIG. 15); conversely, a high signal from the bag sealer 15, 115 may correspond to actuation of the bag sealer to seal the bag B (see steps 206a or 206b in FIG. 15) with the metered amount of foodstuff material F contained therein. A low signal from the foreign object sensor 18, 118 may correspond to a failure of the foreign object sensor 18, 118 to detect detectable material (e.g., the first material M1 associated with the sensor testing implement 52, 152) within the foreign object sensing zone 25, 125; conversely, a high signal from the foreign object sensor 18, 118 may correspond to the detection of detectable material (e.g., the first material M1 associated with the sensor testing implement 52, 152) by the foreign object sensor 18, 118 within the foreign object sensing zone 25, 125 (see steps 205 and 206b in FIG. 15). For example, if the foreign object sensor 18, 118 detects the first material M1, the controller 30, 130 may receive and/or process a high signal from the foreign object sensor 18, 118.

The corresponding exemplary views of signal diagrams seen by the controller 30, 130 are periodically designated in increments of "1", "2", "3", "4", etc. Each increment may represent a period of time for filling a bag B with foodstuff material F and then subsequently sealing the bag B. When the signal associated with the foreign object sensor 18, 118 is high during a period of filling and/or sealing of any bag B, the particular bag(s) B may be deemed to be (a) "reject bag(s)" (see, e.g., B') as a result of the foreign object sensor 18, 118 detecting detectable material (e.g., the first material M1 associated with the sensor testing implement 52, 152) within the foreign object sensing zone 25, 125 (see steps 205 and 206b in FIG. 15). When any bag B is deemed to be a reject bag B', the controller 30, 130 may send a signal to the sealed bag processing portion 22, 122 for executing an act of rejecting (see step 208b in FIG. 15) the reject bag(s) B'.

In an example, as seen in FIGS. 12B-12C, a third (see corresponding signal diagram periods between "2" and "3") formed, filled and sealed bag prepared by the food bagging portion 14, 114 is deemed to be a reject bag B'. As a result, the sealed bag processing portion 22, 122 may include a bag marking device 26, 126 that provides (by way of, e.g., a spray nozzle connected to an ink reservoir included with the structure of the bag marking device 26, 126) one or more markings (see, e.g., "X") upon the reject bag B' (see step 208b in FIG. 15). In some examples, the one or more markings may include, for example, indicia (e.g., letters and/or numbers) prepared with visible ink in order to provide a visible indicator that the bag is a reject bag B'. In other examples, the one or more markings may include, for example, indicia (e.g., letters and/or numbers) prepared with "invisible ink" in order to provide an invisible indicator that the third formed, filled and sealed bag is a reject bag B' (e.g., the "invisible ink" may only be viewable when the reject bag B' is positioned under, for example, ultraviolet light). In other examples, the bag marking device 26 may apply a tag (e.g., a radio frequency identification (RFID) tag) to the reject bag B' (see step 208b in FIG. 15).

Although the controller 30, 130 may cause actuation of the sealed bag processing portion 22, 122 as described above, the controller 30, 130 may actuate other portions of the food processing system 10, 100 in response to the foreign object sensor 18, 118 detecting detectable material (e.g., the first material M1 associated with the sensor testing implement 52, 152) within the foreign object sensing zone 25, 125. For example, upon the foreign object sensor 18, 118 detecting detectable material (e.g., the first material M1 associated with the sensor testing implement 52, 152) within the foreign object sensing zone 25, 125 (see steps 205 and 206b in FIG. 15), the controller 30, 130 may optionally send a signal to the foreign object indicator 24, 124 for actuating an alarm (see step 207b in FIG. 15). The alarm may be visual (e.g., a constant light, a flashing light, a strobing light, a spinning light), audible (e.g., a speaker producing a sound) or a combination of a visual indicator and an audible indicator.

Figure 13A:
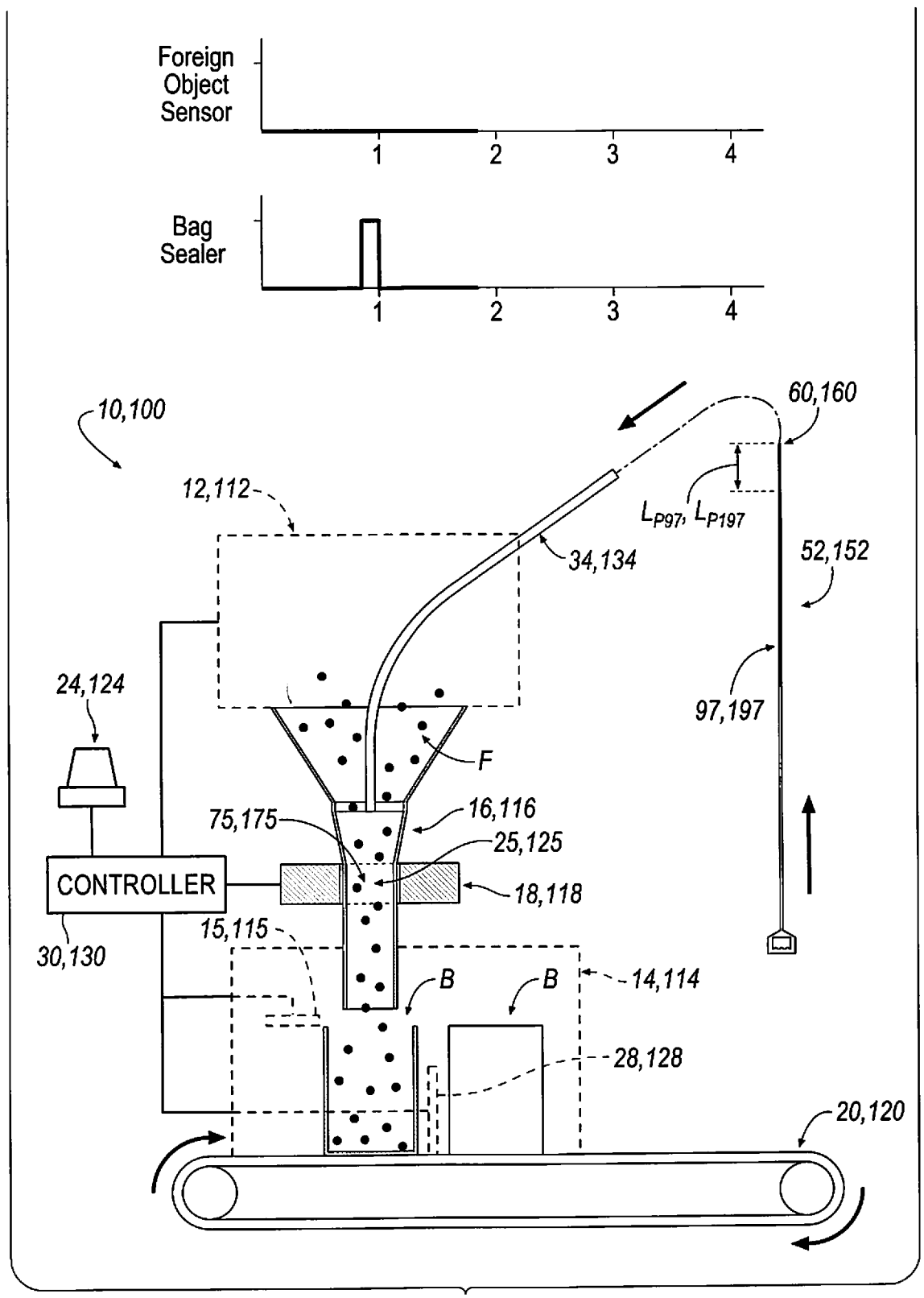
FIG. 13A is a side, partial cross-sectional view of a portion of the food processing system of FIG. 1 or FIG. 2 illustrating the sensor testing implement arranged in a retracted orientation.
Figure 13B:
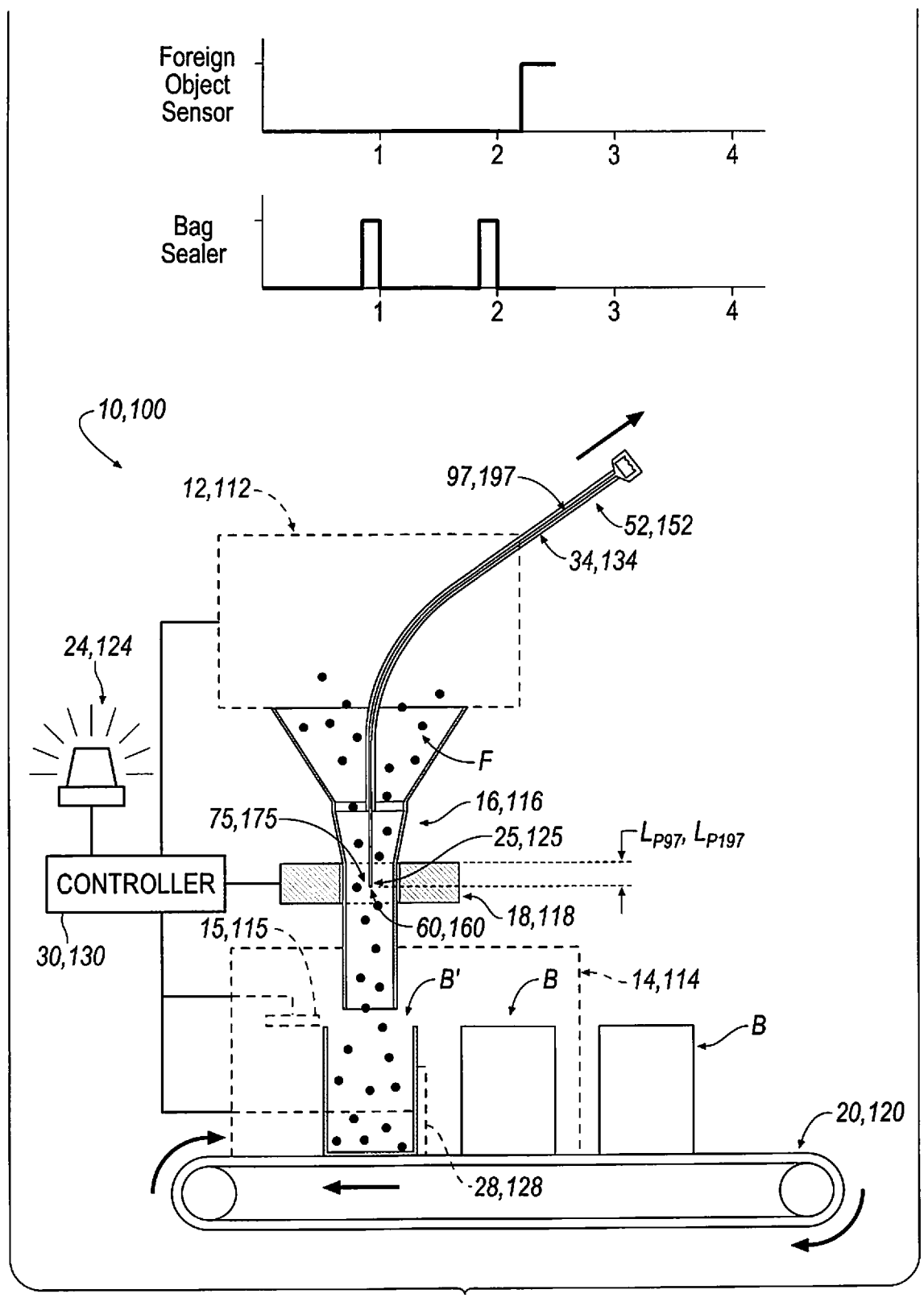
FIG. 13B is a side, partial cross-sectional view of a portion of the food processing system of FIG. 1 or FIG. 2 illustrating the sensor testing implement arranged in a deployed orientation.
Figure 13C:
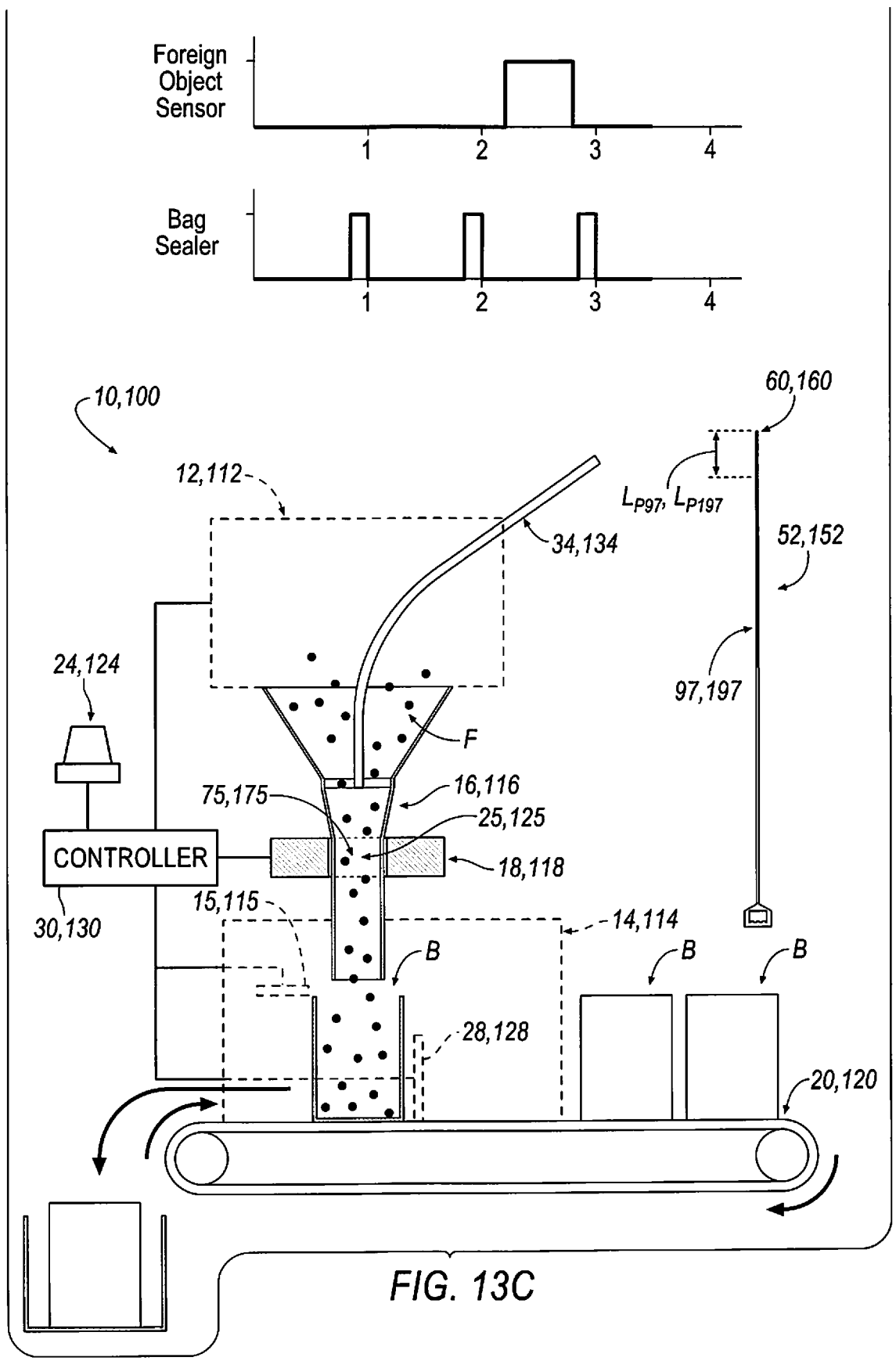
FIG. 13C is a side, partial cross-sectional view of a portion of the food processing system of FIG. 1 or FIG. 2 illustrating the sensor testing implement returned to the retracted orientation.

Referring to FIGS. 13A-13C, an exemplary methodology (see also 200 in FIG. 15) for operating either of the food processing systems 10, 100 is shown. Firstly, the food bagging portion 14, 114 may form a bag B having a sealed lower end and an open, non-sealed upper end (see step 201 in FIG. 15). The scaling portion 12, 112 meters a desired amount of foodstuff material F that is subsequently received at the food bagging portion 14, 114 (see step 202 in FIG. 15). The chute portion 16, 116 guides the metered amount of the foodstuff material F from the scaling portion 12, 112 to the food bagging portion 14, 114 (see step 203 in FIG. 15).

The open, non-sealed upper end of the bag B receives the metered amount of foodstuff material F from the chute portion 16, 116. Once the metered amount of foodstuff material F is disposed within the bag, the bag B may be said to be filled with the foodstuff material F (see step 204 in FIG. 15); then, the controller 30, 130 actuates a sealer 15, 115 of the food bagging portion 14, 114 for sealing and therefore closing the open, non-sealed upper end of the bag B (see step 206a in FIG. 15). Once the upper end of the bag B is sealed, the controller 30, 130 actuates the conveyor portion 20, 120 for shuttling the formed, filled and sealed bag B away from the food bagging portion 14, 114 (see step 207a in FIG. 15). After shuttling the formed, filled and sealed bag B away from the food bagging portion 14, 114, the food bagging portion 14, 114 may form another bag B having a sealed lower end and an open, non-sealed, upper end and repeat the above-described steps in a looped manner.

Referring to FIGS. 13A-13B, at any time during the operation of the food processing system 10, 100, the sensor testing implement 52, 152 may be plunged into the sensor testing conduit 34, 134 (see step 205 in FIG. 15, which occurs after the bag B has been filled with the foodstuff material F at step 204 in FIG. 15) such that: (1) the distal end 60, 160 of the shaft portion 97, 197 may be spatially arranged substantially in the spatial center 75, 175 of the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 may be spatially arranged in the foreign object sensing zone 25, 125 in order to purposefully actuate/ test the foreign object sensor 18, 118. Then, as seen in FIGS.

13B-13C, at any time during the operation of the food processing system 10, 100, the sensor testing implement 52, 152 may be at least partially retracted from the sensor testing conduit 34, 134 such that: (1) the distal end 60, 160 of the shaft portion 97, 197 may not be spatially arranged substantially in the spatial center 75, 175 of the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 is not spatially arranged in the foreign object sensing zone 25, 125.

As seen in FIGS. 13A-13C, corresponding exemplary views of signal diagrams seen by the controller 30, 130 are shown for the foreign object sensor 18, 118 and the bag sealer 15, 115. When the signal associated with actuation of the bag sealer 15, 115 is low, a formed bag B is being filled with foodstuff material F (see step 204 in FIG. 15); conversely, when the signal associated with actuation of the bag sealer 15, 115 is high, the formed bag B is sealed (see steps 206a or 206b in FIG. 15) with the metered amount of foodstuff material F contained therein. When the signal associated with the foreign object sensor 18, 118 is low, the foreign object sensor 18, 118 does not detect detectable material (e.g., the first material M1 associated with the sensor testing implement 52, 152) within the foreign object sensing zone 25, 125; conversely, when the signal associated with the foreign object sensor 18, 118 is high, the foreign object sensor 18, 118 detects detectable material (e.g., the first material M1 associated with the sensor testing implement 52, 152) within the foreign object sensing zone 25, 125 (see steps 205 and 206b in FIG. 15).

The corresponding exemplary views of signal diagrams seen by the controller 30, 130 are periodically designated in increments of "1", "2", "3", "4", etc. Each increment represents a period of time for filling a bag B with foodstuff material F and then subsequently sealing the bag B. When the signal associated with the foreign object sensor 18, 118 is high during a period of filling and sealing of any bag B, that/those particular bag(s) B is/are deemed to be (a) "reject bag(s)" (see, e.g., B') as a result of the foreign object sensor 18, 118 detecting detectable material (e.g., the first material M1 associated with the sensor testing implement 52, 152) within the foreign object sensing zone 25, 125 (see steps 205 and 206b in FIG. 15). Therefore, when any bag B is deemed to be a reject bag B', the controller 30, 130 sends a signal to the sealed bag processing portion 22, 122 for executing an act of rejecting (see step 208b in FIG. 15) the reject bag(s) B'.

In an example, as seen in FIGS. 13B-13C a third (see corresponding signal diagram periods between "2" and "3") formed, filled and sealed bag prepared by the food bagging portion 14, 114 is deemed to be a reject bag B'. As a result, the sealed bag processing portion 22, 122 may include a bag rejecting device 28, 128 (such as, for example, a lever or robotic arm) that removes the reject bag B' from the conveyor portion 20, 120 (see step 208b in FIG. 15) such that the reject bag B' is not comingled with non-rejected formed, filled and sealed bags B that are conveyed away from the food bagging portion 14, 114 by the conveyor portion 20, 120. As seen in FIG. 13C, the bag rejecting device 28, 128 may direct the reject bag B' into a reject bag container C.

Although the controller 30, 130 may cause actuation of the sealed bag processing portion 22, 122 as described above, the controller 30, 130 may actuate other portions of the food processing system 10, 100 in response to the foreign object sensor 18, 118 detecting detectable material (e.g., the first material M1 associated with the sensor testing implement 52, 152) within the foreign object sensing zone 25, 125. For example, upon the foreign object sensor 18, 118 detecting detectable material (e.g., the first material M1 associated with the sensor testing implement 52, 152) within the foreign object sensing zone 25, 125 (see steps 205 and 206b in FIG. 15), the controller 30, 130 may optionally send a signal to the foreign object indicator 24, 124 for actuating an alarm (see step 207b in FIG. 15). The alarm may be visual (e.g., a constant light, a flashing light, a strobing light, a spinning light), audible (e.g., a speaker producing a sound) or a combination or a visual indicator and an audible indicator.

Figure 14A:
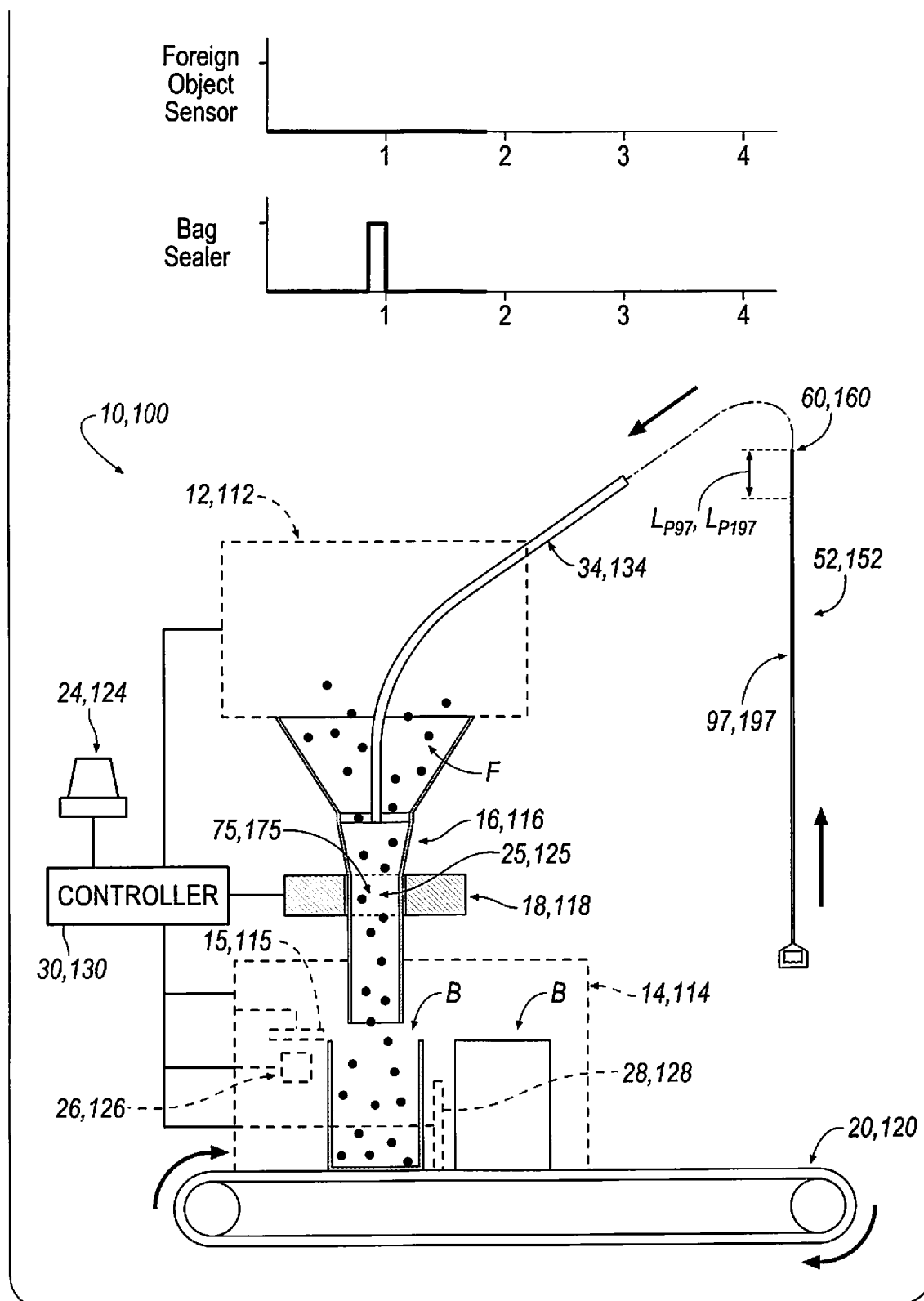
FIG. 14A is a side, partial cross-sectional view of a portion of the food processing system of FIG. 1 or FIG. 2 illustrating the sensor testing implement arranged in a retracted orientation.
Figure 14B:
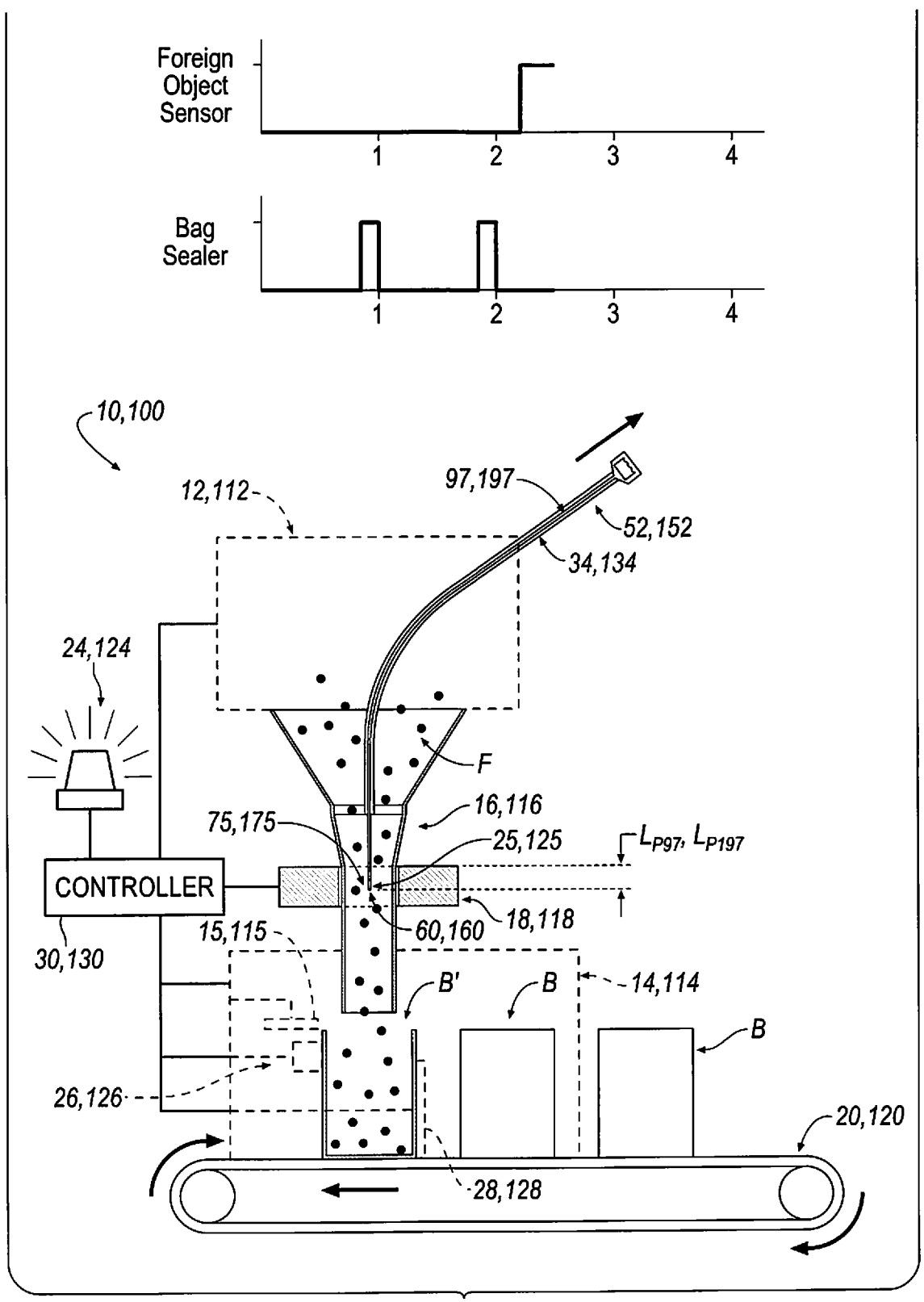
FIG. 14B is a side, partial cross-sectional view of a portion of the food processing system of FIG. 1 or FIG. 2 illustrating the sensor testing implement arranged in a deployed orientation.
Figure 14C:
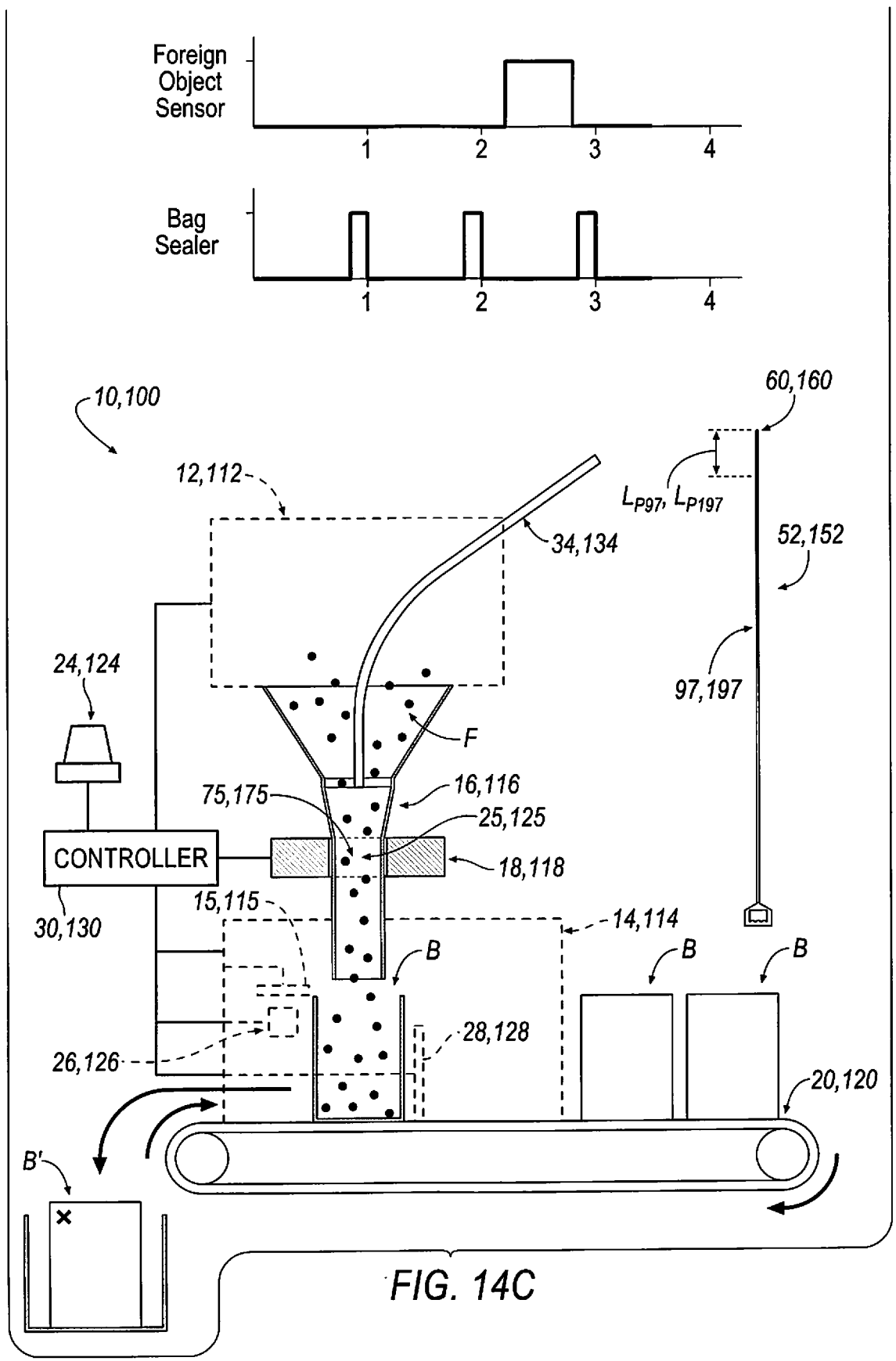
FIG. 14C is a side, partial cross-sectional view of a portion of the food processing system of FIG. 1 or FIG. 2 illustrating the sensor testing implement returned to the retracted orientation.

Referring to FIGS. 14A-14C, an exemplary methodology (see also 200 in FIG. 15) for operating either of the food processing systems 10, 100 is shown. Firstly, the food bagging portion 14, 114 may form a bag B having a sealed lower end and an open non-sealed, upper end (see step 201 in FIG. 15). The scaling portion 12, 112 meters a desired amount of foodstuff material F that is subsequently received at the food bagging portion 14, 114 (see step 202 in FIG. 15). The chute portion 16, 116 guides the metered amount of the foodstuff material F from the scaling portion 12, 112 to the food bagging portion 14, 114 (see step 203 in FIG. 15).

The open, non-sealed upper end of the bag B receives the metered amount of foodstuff material F from the chute portion 16, 116. Once the metered amount of foodstuff material F is disposed within the bag, the bag B may be said to be filled with the foodstuff material F (see step 204 in FIG. 15); then, the controller 30, 130 actuates a sealer 15, 115 of the food bagging portion 14, 114 for sealing and therefore closing the open, non-sealed upper end of the bag B (see step 206a in FIG. 15). Once the upper end of the bag B is sealed, the controller 30, 130 actuates the conveyor portion 20, 120 for shuttling the formed, filled and sealed bag B away from the food bagging portion 14, 114 (see step 207a in FIG. 15). After shuttling the formed, filled and sealed bag B away from the food bagging portion 14, 114, the food bagging portion 14, 114 may form another bag B having a sealed lower end and an open, non-sealed upper end and repeat the above-described steps in a looped manner.

Referring to FIGS. 14A-14B, at any time during the operation of the food processing system 10, 100, the sensor testing implement 52, 152 may be plunged into the sensor testing conduit 34, 134 (see step 205 in FIG. 15, which occurs after the bag B has been filled with the foodstuff material F at step 204 in FIG. 15) such that: (1) the distal end 60, 160 of the shaft portion 97, 197 may be spatially arranged substantially in the spatial center 75, 175 of the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 may be spatially arranged in the foreign object sensing zone 25, 125 in order to purposefully actuate/test the foreign object sensor 18, 118. Then, as seen in FIGS. 14B-14C, at any time during the operation of the food processing system 10, 100, the sensor testing implement 52, 152 may be at least partially retracted from the sensor testing conduit 34, 134 such that: (1) the distal end 60, 160 of the shaft portion 97, 197 may not be spatially arranged substantially in the spatial center 75, 175 of the foreign object sensing zone 25, 125, or (2) the portion $L_{P97}$, $L_{P197}$ of the length $L_{97}$, $L_{197}$ of the shaft portion 97, 197 extending away from the distal end 60, 160 of the shaft portion 97, 197 is not spatially arranged in the foreign object sensing zone 25, 125.

As seen in FIGS. 14A-14C, corresponding exemplary views of signal diagrams seen by the controller 30, 130 are shown for the foreign object sensor 18, 118 and the bag sealer 15, 115. When the signal associated with actuation of the bag sealer 15, 115 is low, a formed bag B is being filled with foodstuff material F (see step 204 in FIG. 15); conversely, when the signal associated with actuation of the bag sealer 15, 115 is high, the formed bag B is sealed (see steps 206a or 206b in FIG. 15) with the metered amount of foodstuff material F contained therein. When the signal associated with the foreign object sensor 18, 118 is low, the foreign object sensor 18, 118 does not detect detectable material (e.g., the first material M1 associated with the sensor testing implement 52, 152) within the foreign object sensing zone 25, 125; conversely, when the signal associated with the foreign object sensor 18, 118 is high, the foreign object sensor 18, 118 detects detectable material (e.g., the first material M1 associated with the sensor testing implement 52, 152) within the foreign object sensing zone 25, 125 (see steps 205 and 206b in FIG. 15).

The corresponding exemplary views of signal diagrams seen by the controller 30, 130 are periodically designated in increments of "1", "2", "3", "4", etc. Each increment represents a period of time for filling a bag B with foodstuff material F and then subsequently sealing the bag B. When the signal associated with the foreign object sensor 18, 118 is high during a period of filling and sealing of any bag B, that/those particular bag(s) B is/are deemed to be (a) "reject bag(s)" (see, e.g., B') as a result of the foreign object sensor 18, 118 detecting detectable material (e.g., the first material M1 associated with the sensor testing implement 52, 152) within the foreign object sensing zone 25, 125 (see steps 205 and 206b in FIG. 15). Therefore, when any bag B is deemed to be a reject bag B', the controller 30, 130 sends a signal to the sealed bag processing portion 22, 122 for executing an act of rejecting (see step 208b in FIG. 15) the reject bag(s) B'.

In an example, as seen in FIGS. 14B-14C a third (see corresponding signal diagram periods between "2" and "3") formed, filled and sealed bag prepared by the food bagging portion 14, 114 is deemed to be a reject bag B'. As a result, the sealed bag processing portion 22, 122 may include a bag marking device 26, 126 that provides (by way of, e.g., a spray nozzle connected to an ink reservoir included with the structure of the bag marking device 26, 126) one or more markings (see, e.g., "X") upon the reject bag B' (see step 208b in FIG. 15). In some examples, the one or more markings may include, for example, indicia (e.g., letters and/or numbers) prepared with visible ink in order to provide a visible indicator that the bag is a reject bag B'. In other examples, the one or more markings may include, for example, indicia (e.g., letters and/or numbers) prepared with "invisible ink" in order to provide an invisible indicator that the third formed, filled and sealed bag is a reject bag B' (e.g., the "invisible ink" may only be viewable when the reject bag B' is positioned under, for example, ultraviolet light). In other examples, the bag marking device 26 may apply a tag (e.g., a radio frequency identification (RFID) tag) to the reject bag B' (see step 208b in FIG. 15).

In addition to the bag marking device 26, 126, the sealed bag processing portion 22, 122 may also include the bag rejecting device 28, 128 (such as, for example, a lever or robotic arm) that removes the marked reject bag B' from the conveyor portion 20, 120 (see step 208b in FIG. 15) such that the marked reject bag B' is not comingled with non-marked, non-rejected formed, filled and sealed bags B that are conveyed away from the food bagging portion 14, 114 by the conveyor portion 20, 120. As seen in FIG. 14C, the bag rejecting device 28, 128 may direct the marked reject bag B' into a marked reject bag container C.

Although the controller 30, 130 may cause actuation of the sealed bag processing portion 22, 122 as described above, the controller 30, 130 may actuate other portions of the food processing system 10, 100 in response to the foreign object sensor 18, 118 detecting detectable material (e.g., the first material M1 associated with the sensor testing implement 52, 152) within the foreign object sensing zone 25, 125. For example, upon the foreign object sensor 18, 118 detecting detectable material (e.g., the first material M1 associated with the sensor testing implement 52, 152) within the foreign object sensing zone 25, 125 (see steps 205 and 206b in FIG. 15), the controller 30, 130 may optionally send a signal to the foreign object indicator 24, 124 for actuating an alarm (see step 207b in FIG. 15). The alarm may be visual (e.g., a constant light, a flashing light, a strobing light, a spinning light), audible (e.g., a speaker producing a sound) or a combination or a visual indicator and an audible indicator.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method comprising:
   providing a food processing system including:
   a chute portion including a chute body defining a passage;
   a foreign object sensor adjacent to the chute portion, wherein the foreign object sensor and the chute portion cooperatively form a foreign object sensing zone within the passage;
   a sensor testing conduit having a first end defining an entrance opening disposed outside of the chute body and a second end defining an exit opening disposed within the passage adjacent to or within the foreign object sensing zone; and
   a sensor testing implement including a shaft extending from a first end to a second end, the second end of the shaft of the sensor testing implement configured to be selectively inserted through the passage of the sensor testing conduit and into the foreign object sensing zone;
   forming a bag;
   metering an amount of foodstuff material into the bag through the chute body;
   while the amount of foodstuff material is metered into the bag;

inserting the shaft of the sensor testing implement through the sensor testing conduit via the entrance opening, whereby the second end of the shaft extends from the exit opening and is positioned within the foreign object sensing zone; and utilizing the foreign object sensor for monitoring for presence of the sensor testing implement within the foreign object sensing zone; and processing the bag as a reject bag when the foreign object sensor does not detect the presence of the sensor testing implement within the foreign object sensing zone.

2. The method according to claim 1 further comprising:

utilizing a food scaling portion for metering the amount of foodstuff material;

utilizing a food bagging portion for forming the bag; and utilizing the chute portion for guiding the amount of foodstuff material, wherein the chute: portion connects the food scaling portion to the food bagging portion; and arranging the foreign object sensor about the chute portion.

3. The method according to claim 1, wherein processing the bag as the reject bag includes:

sealing an open, non-sealed upper end of the bag; and conveying the sealed bag to another location.

4. The method according to claim 1, wherein the processing the sealed bag includes removing the reject bag from a conveyor portion.

5. The method according to claim 1, wherein processing the bag as the reject bag includes spraying the reject bag with an ink indicating that the bag is the reject bag.

6. The method according to claim 1, further comprising, when the foreign object sensor does not detect the presence of the sensor testing implement, actuating an alarm.

7. A method comprising:

forming a bag;

metering an amount of foodstuff material into the bag through a chute portion;

while the amount of foodstuff material is metered into the bag;

inserting a shaft of a sensor testing implement through a sensor testing conduit disposed within the chute portion, a first end of the sensor testing implement being arranged within the chute portion and a second end of the shaft being arranged outside of the chute portion, and utilizing a foreign object sensor for monitoring for presence of the sensor testing implement deliberately in a foreign object sensing zone formed by the foreign object sensor;

withdrawing the sensor testing implement from the foreign object sensing zone through the sensor testing conduit; and processing the bag as a reject bag when the foreign object sensor does not detect the presence of the sensor testing implement inserted within the foreign object sensing zone.

* * * * *